US008822155B2

(12) United States Patent
Sukumar et al.

(10) Patent No.: US 8,822,155 B2
(45) Date of Patent: *Sep. 2, 2014

(54) QUANTITATIVE MULTIPLEX METHYLATION-SPECIFIC PCR

(75) Inventors: Saraswati Sukumar, Columbia, MD (US); Mary Jo Fackler, Hunt Valley, MD (US); Theresa Swift-Scanlan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/224,024

(22) Filed: Sep. 1, 2011

(65) Prior Publication Data

US 2014/0220561 A1 Aug. 7, 2014

Related U.S. Application Data

(63) Continuation of application No. 10/976,932, filed on Oct. 28, 2004, now Pat. No. 8,062,849.

(60) Provisional application No. 60/515,100, filed on Oct. 28, 2003.

(51) Int. Cl.
*C12Q 1/68* (2006.01)
*C12P 19/34* (2006.01)

(52) U.S. Cl.
USPC ......................................... 435/6.12; 435/91.2

(58) Field of Classification Search
None
See application file for complete search history.

(56) References Cited

U.S. PATENT DOCUMENTS

| 8,062,849 | B2 * | 11/2011 | Sukumar et al. ............. | 435/6.12 |
| 2003/0143606 | A1 | 7/2003 | Olek et al. | |
| 2005/0089862 | A1 | 4/2005 | Therianos et al. | |

OTHER PUBLICATIONS

Brock et al., "Prognostic Importance of Promoter Hypermethylation of Multiple Genes in Esophageal Adenocarcinoma", *Clinical Cancer Research*, 9:2912-2919 (2003).
Buck et al., "Design strategies and performance of custom DNA sequencing primers", *Biotechniques*, 27(3):528-536 (1999).
Buller et al., "Validation of a Multiplex Methylation-Sensitive PCR Assay for the Diagnosis of Prader-Willi and Angelman's Syndromes", *Molecular Diagnosis*, 5(3):239-243 (2000).
Burbee et al., "Epigenetic Inactivation of RASSF1A in Lung and Breast Cancers and Malignant Phenotype Suppression", *Journal of the National Cancer Institute*, 93(9):6910-699 (2001).
Dammann et al., "Hypermethylation of the CpG Island of Ras Association Domain Family 1A (RASSF1A), a Putative Tumor Suppressor Gene from the 3p21.3 Locus, Occurs in a Large Percentage of Human Breast Cancers", *Cancer Research*, 61:3105-3109 (2001).

Dhar et al., "Analysis of Normal Epithelial Cell Specific-1 (NES1)/Kallikrein 10 mRNA Expression by in Situ Hybrdization, a Novel Marker for Breast Cancer", *Clinical Cancer Research*, 7:3393-3398 (2001).
Eads et al., "MethylLight: a high-throughput assay to measure DNA methylation", *Nucleic Acids Res.*, 28(8):e32, i-viii (2000).
Evron et al., "Detection of Breast Cancer Cells in Ductal Lavage Fluid by Methylation-specific PCR", *The Lancet*, 357:1335-1336 (2001).
Evron et al., "Loss of Cyclin D2 Expression in the Majority of Breast Cancers is Associated with Promoter Hypermethylation", *Cancer Research*, 61:2782-2787 (2001).
Fackler et al., "DNA Methylation of RASSF1A, HIN-1, RAR-beta, Cyclin D2 and TWIST in In Situ and Invasive Lobular Breast Carcinoma", *Int J Cancer*, 107:970-975, 2003.
Fackler et al., "Quantitative Multiplex Methylation-Specific PCR Assay for the Detection of Promoter Hypermethylation in Multiple Genes in Breast Cancer", *Cancer Res.*, 64:4442-4452 (2004).
Goessl et al., "Fluorescent Methylation-specific Polymerase Chain Reaction for DNA-based Detection of Prostate Cancer in Bodily Fluids", *Cancer Res.*, 60:5941-5945 (2000).
Goyal et al., "The Role for NES1 Serine Protease as a Novel Tumor Suppressor", *Cancer Research*, 58:4782-4786 (1998).
Herman et al., "Methylation-Sepcific PCR: A Novel PCR Assay for Methylation Status of CpG Islands", *Proc. Natl. Acad. Sci.*, 93:9821-9826 (1996).
Johnson et al., "Plasma nucleic acids in the diagnosis and management of malignant disease", *Clin. Chem.*, 48(8):1186-1193 (2002).
Kashiwaba et al., "Aberrations of the APC Gene in Primary Breast Carcinoma", *J. Cancer Res. Clin. Oncol.*, 120:727-731 (1994).
Krop et al., "HIN-1, a Putative Cytokine Highly Expressed in Normal But Not Cancerous Mammary Epithelial Cells", *PNAS*, 98(17):9796-9801 (2001).
Lehmann et al., "Quantiative Assessment of Promoter Hypermethylation During Breast Cancer Development", *American Journal of Pathology*, 160(2):605-612 (2002).

(Continued)

*Primary Examiner* — Kenneth R. Horlick
*Assistant Examiner* — David Thomas
(74) *Attorney, Agent, or Firm* — DLA Piper LLP (US)

(57) ABSTRACT

Methods are provided for diagnosing in a subject a condition, such as a carcinoma, sarcoma or leukemia, associated with hypermethylation of genes by isolating the genes from tissue containing as few as 50 to 1000 tumor cells. Using quantitative multiplex methylation specific PCR (QM-MSP), multiple genes can be quantitatively evaluated from samples usually yielding sufficient DNA for analysis of only 1 or 2 genes. DNA sequences isolated from the sample are simultaneously co-amplified in an initial multiplex round of PCR, and the methylation status of individual hypermethylation-prone gene promoter sequences is then determined separately or in multiplex using a real time PCR round that is methylation status-specific. Within genes of the panel, the level of promoter hypermethylation as well as the incidence of promoter hypermethylation can be determined and the level of genes in the panel can be scored cumulatively. The QM-MSP method is adaptable for high throughput automated technology.

21 Claims, 13 Drawing Sheets

(56) References Cited

OTHER PUBLICATIONS

Li et al., "CpG Methylation as a Basis for Breast Tumor-Specific Loss of NES1/Kallikrein 10 Expression", Cancer Research, 61:8014-8021 (2001).

Lo et al., "Quantitative Analysis of Aberrant p16 Methylation Using Real-Time Quantitative Methylation-Specific Polymerase Chain Reaction", *Cancer Research*, 59:3899-3903 (1999).

Miyamoto and Ushijima, "Diagnostic and therapeutic applications of epigenetics", *Jpn. J. Clin. Oncol.*, 35(6):293-301 (2005).

Olek et al., GenBank Acession No. AX344838 (2002).

Palmisano et al., "Predicting Lung Cancer by Detecting Aberrant Promoter Methylation in Sputum", *Cancer Research*, 60:5954-5958 (2000).

Sarrio et al., "Epigenetic and Genetic Alternations of APC and CDH1 Genes in Lobular Breast Cancer: Relationships With Abnormal E-Cadherin and Catenin Expression and Microsatellite Instability", *Int. J. Cancer*, 106:208-215 (2003).

Sirchia et al., "Endogenous Reactivation of the RARβ2 Tumor Suppressor Gene Epigenetically Silenced in Breast Cancer", *Cancer Research*, 62:2455-2461 (2002).

Trinh et al., "DNA Methylation Analysis by MethyLight Technology", *Methods*, 25:456-462 (2001).

Virmani et al., "Aberrant Methylation of the Adenomatous Polyposis Coli (APC) Gene Promoter 1A in Breast and Lung Carcinomas", *Clinical Cancer Research*, 7:1998-2004 (2001).

Widschwendter et al., "Methylation and Silencing of the Retinoic Acid Receptor-β2 Gene in Breast Cancer", *Journal of the National Cancer Institute*, 92(10):826-832 (2000).

Wong et al., "Quantiative Analysis of Tumor-Derived Methylated p16INK4a Sequences in Plasma, Serum and Blood Cells of Hepatocellular Carcinoma Subjects", *Clin. Cancer. Res.*, 9:1047-1052 (2003).

Yan et al., "Role of DNA Methylation and Histone Acetylation in Steroid Receptor Expression in Breast Cancer", *Journal of Mammary Gland Biology and Neoplasia*, 6(2):183-192 (2001).

Yunes et al., "Loss of Expression of the Putative Tumor Suppressor NES1 Gene in Biospy-Proven Ductal Carcinoma In Situ Predicts for Invasive Carcinoma At Definitive Surgery", *Int. J. Radiation Oncology Biol. Phys.*, 56(3):653-657 (2003).

\* cited by examiner

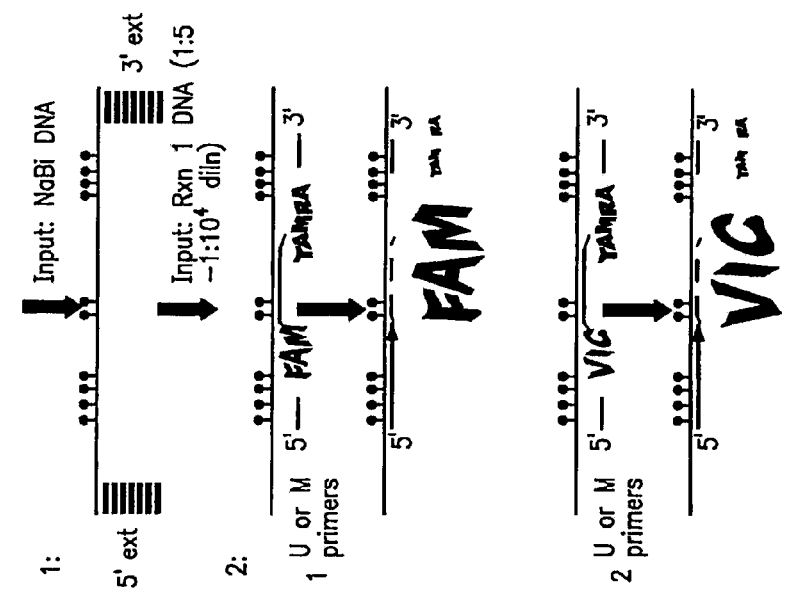
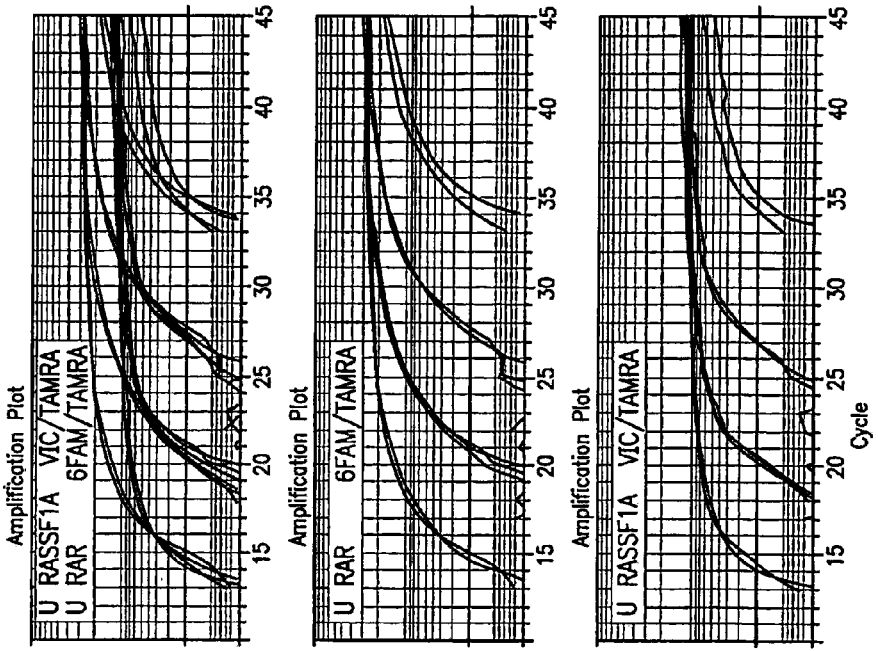
FIG. 1B
FIG. 1A

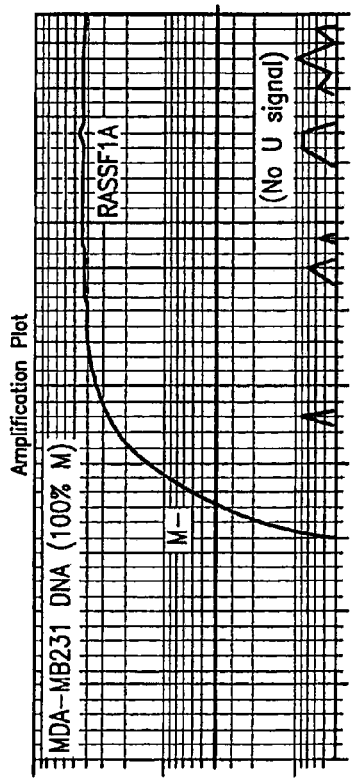
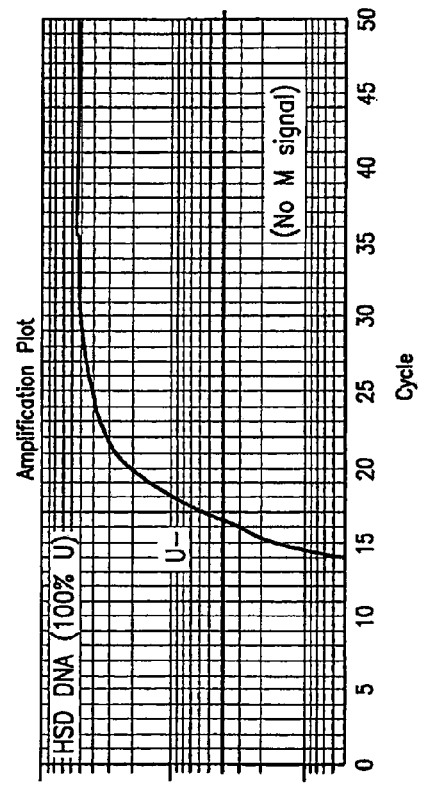
FIG. 3A
FIG. 3B

FIG. 7A  FIG. 7B

| Gene | % Methylation | | | | | | | | | | | |
|---|---|---|---|---|---|---|---|---|---|---|---|---|
| | 3 | | 4 | | 5 | | 6 | | 7 | | 8 | |
| | T | N | T | N | T | N | T | N | T | N | T | N | Ctrl |
| RASSF1A | 1 | 0 | 30 | 4 | 19 | 8 | 63 | 8 | 72 | 7 | 61 | 27 | 100 |
| TWIST | 3 | 1 | 2 | 0 | 17 | 2 | 58 | 5 | 69 | 1 | 61 | 2 | 100 |
| Cyc D2 | 1 | 1 | 0 | 0 | 0 | 0 | 0 | 0 | 9 | 0 | 44 | 0 | 100 |
| HIN 1 | 0 | 0 | 6 | 0 | 72 | 0 | 37 | 4 | 58 | 0 | 92 | 0 | 100 |
| Total | 5 | 2 | 38 | 4 | 108 | 10 | 158 | 17 | 208 | 8 | 258 | 29 | 400 |

SEQUENCE LISTING

<160> NUMBER OF SEQ ID NOS: 93

<210> SEQ ID NO 1
<211> LENGTH: 25
<212> TYPE: DNA
<213> ORGANISM: Artificial sequence

```
<220> FEATURE:
<223> OTHER INFORMATION: Amplification primer

<400> SEQUENCE: 1 tatttttgt aaagatagtt ttgat                                          25

<210> SEQ ID NO 2
<211> LENGTH: 23
<212> TYPE: DNA
<213> ORGANISM: Artificial sequence
<220> FEATURE:
<223> OTHER INFORMATION: Amplification primer

<400> SEQUENCE: 2
tacaactttc taaaaataa ccc                                            23

<210> SEQ ID NO 3
<211> LENGTH: 23
<212> TYPE: DNA
<213> ORGANISM: Artificial sequence
<220> FEATURE:
<223> OTHER INFORMATION: Amplification primer

<400> SEQUENCE: 3
gttttatagt ttttgtattt agg                                           23

<210> SEQ ID NO 4
<211> LENGTH: 22
<212> TYPE: DNA
<213> ORGANISM: Artificial sequence
<220> FEATURE:
<223> OTHER INFORMATION: Amplification primer

<400> SEQUENCE: 4
aactcaataa actcaaactc cc                                            22

<210> SEQ ID NO 5
<211> LENGTH: 21
<212> TYPE: DNA
<213> ORGANISM: Artificial sequence
<220> FEATURE:
<223> OTHER INFORMATION: Amplification primer

<400> SEQUENCE: 5
cctcccaaac cattcaaaaa c                                             21

<210> SEQ ID NO 6
<211> LENGTH: 23
<212> TYPE: DNA
<213> ORGANISM: Artificial sequence
<220> FEATURE:
<223> OTHER INFORMATION: Amplification primer

<400> SEQUENCE: 6
gagatgagat attatttatt gtg                                           23

<210> SEQ ID NO 7
<211> LENGTH: 22
<212> TYPE: DNA
<213> ORGANISM: Artificial sequence
<220> FEATURE:
<223> OTHER INFORMATION: Amplification primer

<400> SEQUENCE: 7
gtaggagggt ttattttttg tt                                            22
```

```
<210> SEQ ID NO 8
<211> LENGTH: 23
<212> TYPE: DNA
<213> ORGANISM: Artificial sequence
<220> FEATURE:
<223> OTHER INFORMATION: Amplification primer

<400> SEQUENCE: 8
aattacattt tccaaactta ctc                                       23

<210> SEQ ID NO 9
<211> LENGTH: 20
<212> TYPE: DNA
<213> ORGANISM: Artificial sequence
<220> FEATURE:
<223> OTHER INFORMATION: Amplification primer

<400> SEQUENCE: 9
gtttgttaag aggaagtttt                                           20

<210> SEQ ID NO 10
<211> LENGTH: 24
<212> TYPE: DNA
<213> ORGANISM: Artificial sequence
<220> FEATURE:
<223> OTHER INFORMATION: Amplification primer

<400> SEQUENCE: 10
ccgaaacata caaaacaaaa ccac                                      24

<210> SEQ ID NO 11
<211> LENGTH: 21
<212> TYPE: DNA
<213> ORGANISM: Artificial sequence
<220> FEATURE:
<223> OTHER INFORMATION: Amplification primer

<400> SEQUENCE: 11
tatataggtt ggggaagttt g                                         21

<210> SEQ ID NO 12
<211> LENGTH: 24
<212> TYPE: DNA
<213> ORGANISM: Artificial sequence
<220> FEATURE:
<223> OTHER INFORMATION: Amplification primer

<400> SEQUENCE: 12
tataaaaaca taaaacctat aacc                                      24

<210> SEQ ID NO 13
<211> LENGTH: 27
<212> TYPE: DNA
<213> ORGANISM: Artificial sequence
<220> FEATURE:
<223> OTHER INFORMATION: Amplification primer

<400> SEQUENCE: 13
tttgatttaa ggatgcgtta gagtacg                                   27

<210> SEQ ID NO 14
<211> LENGTH: 25
<212> TYPE: DNA
<213> ORGANISM: Artificial sequence
<220> FEATURE:
<223> OTHER INFORMATION: Amplification primer
```

```
<400> SEQUENCE: 14
actttctccc taaaaaccga ctacg                                        25

<210> SEQ ID NO 15
<211> LENGTH: 24
<212> TYPE: DNA
<213> ORGANISM: Artificial sequence
<220> FEATURE:
<223> OTHER INFORMATION: Amplification primer

<400> SEQUENCE: 15
aatccgccaa cacgatcgac ccta                                         24

<210> SEQ ID NO 16
<211> LENGTH: 23
<212> TYPE: DNA
<213> ORGANISM: Artificial sequence
<220> FEATURE:
<223> OTHER INFORMATION: Amplification primer

<400> SEQUENCE: 16
ttaaggatgt gttagagtat gtg                                          23

<210> SEQ ID NO 17
<211> LENGTH: 29
<212> TYPE: DNA
<213> ORGANISM: Artificial sequence
<220> FEATURE:
<223> OTHER INFORMATION: Amplification primer

<400> SEQUENCE: 17
aaactttctc cctaaaaacc aactacaat                                    29

<210> SEQ ID NO 18
<211> LENGTH: 26
<212> TYPE: DNA
<213> ORGANISM: Artificial sequence
<220> FEATURE:
<223> OTHER INFORMATION: Amplification primer

<400> SEQUENCE: 18
aatccaccaa cacaatcaac cctaac                                       26

<210> SEQ ID NO 19
<211> LENGTH: 18
<212> TYPE: DNA
<213> ORGANISM: Artificial sequence
<220> FEATURE:
<223> OTHER INFORMATION: Amplification primer

<400> SEQUENCE: 19
gcgttgaagt cggggttc                                                18

<210> SEQ ID NO 20
<211> LENGTH: 24
<212> TYPE: DNA
<213> ORGANISM: Artificial sequence
<220> FEATURE:
<223> OTHER INFORMATION: Amplification primer

<400> SEQUENCE: 20
cccgtacttc gctaacttta aacg                                         24

<210> SEQ ID NO 21
```

```
<211> LENGTH: 24
<212> TYPE: DNA
<213> ORGANISM: Artificial sequence
<220> FEATURE:
<223> OTHER INFORMATION: Amplification primer

<400> SEQUENCE: 21
acaaacgcga accgaacgaa acca                                          24

<210> SEQ ID NO 22
<211> LENGTH: 20
<212> TYPE: DNA
<213> ORGANISM: Artificial sequence
<220> FEATURE:
<223> OTHER INFORMATION: Amplification primer

<400> SEQUENCE: 22
ggtgttgaag ttggggtttg                                               20

<210> SEQ ID NO 23
<211> LENGTH: 23
<212> TYPE: DNA
<213> ORGANISM: Artificial sequence
<220> FEATURE:
<223> OTHER INFORMATION: Amplification primer

<400> SEQUENCE: 23
cccatacttc actaacttta aac                                           23

<210> SEQ ID NO 24
<211> LENGTH: 27
<212> TYPE: DNA
<213> ORGANISM: Artificial sequence
<220> FEATURE:
<223> OTHER INFORMATION: Amplification primer

<400> SEQUENCE: 24
ctaacaaaca caaaccaaac aaaacca                                       27

<210> SEQ ID NO 25
<211> LENGTH: 22
<212> TYPE: DNA
<213> ORGANISM: Artificial sequence
<220> FEATURE:
<223> OTHER INFORMATION: Amplification primer

<400> SEQUENCE: 25
gttagggttc gggggcgttg tt                                            22

<210> SEQ ID NO 26
<211> LENGTH: 21
<212> TYPE: DNA
<213> ORGANISM: Artificial sequence
<220> FEATURE:
<223> OTHER INFORMATION: Amplification primer

<400> SEQUENCE: 26
ccgtcgcctt cctccgacga a                                             21

<210> SEQ ID NO 27
<211> LENGTH: 24
<212> TYPE: DNA
<213> ORGANISM: Artificial sequence
<220> FEATURE:
<223> OTHER INFORMATION: Amplification primer

<400> SEQUENCE: 27
```

```
aaacgatttc cttccccgcc gaaa                                              24

<210> SEQ ID NO 28
<211> LENGTH: 23
<212> TYPE: DNA
<213> ORGANISM: Artificial sequence
<220> FEATURE:
<223> OTHER INFORMATION: Amplification primer

<400> SEQUENCE: 28
ggtttggggg tgttgtttgt atg                                               23

<210> SEQ ID NO 29
<211> LENGTH: 21
<212> TYPE: DNA
<213> ORGANISM: Artificial sequence
<220> FEATURE:
<223> OTHER INFORMATION: Amplification primer

<400> SEQUENCE: 29
cccacctcct aaccaccctc c                                                 21

<210> SEQ ID NO 30
<211> LENGTH: 26
<212> TYPE: DNA
<213> ORGANISM: Artificial sequence
<220> FEATURE:
<223> OTHER INFORMATION: Amplification primer

<400> SEQUENCE: 30
aaacaatttc cttcccacc aaaaca                                             26

<210> SEQ ID NO 31
<211> LENGTH: 22
<212> TYPE: DNA
<213> ORGANISM: Artificial sequence
<220> FEATURE:
<223> OTHER INFORMATION: Amplification primer

<400> SEQUENCE: 31
agaacgcgag cgattcgagt ag                                                22

<210> SEQ ID NO 32
<211> LENGTH: 24
<212> TYPE: DNA
<213> ORGANISM: Artificial sequence
<220> FEATURE:
<223> OTHER INFORMATION: Amplification primer

<400> SEQUENCE: 32
tacaaaaaac cttccgaata cgtt                                              24

<210> SEQ ID NO 33
<211> LENGTH: 24
<212> TYPE: DNA
<213> ORGANISM: Artificial sequence
<220> FEATURE:
<223> OTHER INFORMATION: Amplification primer

<400> SEQUENCE: 33
atcctacccc gacgataccc aaac                                              24

<210> SEQ ID NO 34
<211> LENGTH: 25
<212> TYPE: DNA
```

<213> ORGANISM: Artificial sequence
<220> FEATURE:
<223> OTHER INFORMATION: Amplification primer

<400> SEQUENCE: 34
ttgagaatgt gagtgatttg agtag                                 25

<210> SEQ ID NO 35
<211> LENGTH: 26
<212> TYPE: DNA
<213> ORGANISM: Artificial sequence
<220> FEATURE:
<223> OTHER INFORMATION: Amplification primer

<400> SEQUENCE: 35
ttacaaaaaa ccttccaaat acattc                                26

<210> SEQ ID NO 36
<211> LENGTH: 26
<212> TYPE: DNA
<213> ORGANISM: Artificial sequence
<220> FEATURE:
<223> OTHER INFORMATION: Amplification primer

<400> SEQUENCE: 36
aaatcctacc ccaacaatac ccaaac                                26

<210> SEQ ID NO 37
<211> LENGTH: 21
<212> TYPE: DNA
<213> ORGANISM: Artificial sequence
<220> FEATURE:
<223> OTHER INFORMATION: Amplification primer

<400> SEQUENCE: 37
tagggaaggg ggtacgggtt t                                     21

<210> SEQ ID NO 38
<211> LENGTH: 20
<212> TYPE: DNA
<213> ORGANISM: Artificial sequence
<220> FEATURE:
<223> OTHER INFORMATION: Amplification primer

<400> SEQUENCE: 38
cgctcacgac cgtaccctaa                                       20

<210> SEQ ID NO 39
<211> LENGTH: 24
<212> TYPE: DNA
<213> ORGANISM: Artificial sequence
<220> FEATURE:
<223> OTHER INFORMATION: Amplification primer

<400> SEQUENCE: 39
acttcctact acgaccgacg aacc                                  24

<210> SEQ ID NO 40
<211> LENGTH: 24
<212> TYPE: DNA
<213> ORGANISM: Artificial sequence
<220> FEATURE:
<223> OTHER INFORMATION: Amplification primer

<400> SEQUENCE: 40 aagttttga ggtttgggta ggga                                   24

<210> SEQ ID NO 41
<211> LENGTH: 22
<212> TYPE: DNA
<213> ORGANISM: Artificial sequence
<220> FEATURE:
<223> OTHER INFORMATION: Amplification primer

<400> SEQUENCE: 41
accaacctca cccacactcc ta                                              22

<210> SEQ ID NO 42
<211> LENGTH: 26
<212> TYPE: DNA
<213> ORGANISM: Artificial sequence
<220> FEATURE:
<223> OTHER INFORMATION: Amplification primer

<400> SEQUENCE: 42
caacttccta ctacaaccaa caaacc                                          26

<210> SEQ ID NO 43
<211> LENGTH: 25
<212> TYPE: DNA
<213> ORGANISM: Artificial sequence
<220> FEATURE:
<223> OTHER INFORMATION: Amplification primer

<400> SEQUENCE: 43
tggtgatgga ggaggtttag taagt                                           25

<210> SEQ ID NO 44
<211> LENGTH: 27
<212> TYPE: DNA
<213> ORGANISM: Artificial sequence
<220> FEATURE:
<223> OTHER INFORMATION: Amplification primer

<400> SEQUENCE: 44
aaccaataaa acctactcct cccttaa                                         27

<210> SEQ ID NO 45
<211> LENGTH: 30
<212> TYPE: DNA
<213> ORGANISM: Artificial sequence
<220> FEATURE:
<223> OTHER INFORMATION: Amplification primer

<400> SEQUENCE: 45
accaccaccc aacacacaat aacaaacaca                                      30

<210> SEQ ID NO 46
<211> LENGTH: 22
<212> TYPE: DNA
<213> ORGANISM: Artificial sequence
<220> FEATURE:
<223> OTHER INFORMATION: Amplification primer

<400> SEQUENCE: 46
ggtgtatttg gatagtagta ag                                              22

<210> SEQ ID NO 47
<211> LENGTH: 23
<212> TYPE: DNA
<213> ORGANISM: Artificial sequence
<220> FEATURE:

<223> OTHER INFORMATION: Amplification primer

<400> SEQUENCE: 47
ctccaaataa taaaacacct act                                         23

<210> SEQ ID NO 48
<211> LENGTH: 20
<212> TYPE: DNA
<213> ORGANISM: Artificial sequence
<220> FEATURE:
<223> OTHER INFORMATION: Amplification primer

<400> SEQUENCE: 48 aaaccctat accccactac                                              20

<210> SEQ ID NO 49
<211> LENGTH: 24
<212> TYPE: DNA
<213> ORGANISM: Artificial sequence
<220> FEATURE:
<223> OTHER INFORMATION: Amplification primer

<400> SEQUENCE: 49
ggttgtatta atatagttat atgt                                        24

<210> SEQ ID NO 50
<211> LENGTH: 23
<212> TYPE: DNA
<213> ORGANISM: Artificial sequence
<220> FEATURE:
<223> OTHER INFORMATION: Amplification primer

<400> SEQUENCE: 50
tattttgaga ggttgttgtt tag                                         23

<210> SEQ ID NO 51
<211> LENGTH: 22
<212> TYPE: DNA
<213> ORGANISM: Artificial sequence
<220> FEATURE:
<223> OTHER INFORMATION: Amplification primer

<400> SEQUENCE: 51
aaacatcact taaaccccct at                                          22

<210> SEQ ID NO 52
<211> LENGTH: 22
<212> TYPE: DNA
<213> ORGANISM: Artificial sequence
<220> FEATURE:
<223> OTHER INFORMATION: Amplification primer

<400> SEQUENCE: 52
gttgggatgt ttgataagga at                                          22

<210> SEQ ID NO 53
<211> LENGTH: 21
<212> TYPE: DNA
<213> ORGANISM: Artificial sequence
<220> FEATURE:
<223> OTHER INFORMATION: Amplification primer

<400> SEQUENCE: 53
atcacaaatc tatcccctca c                                           21

<210> SEQ ID NO 54
<211> LENGTH: 19
<212> TYPE: DNA
<213> ORGANISM: Artificial sequence
<220> FEATURE:
<223> OTHER INFORMATION: Amplification primer

<400> SEQUENCE: 54
aaagaggagg ggttggttg                                              19

<210> SEQ ID NO 55
<211> LENGTH: 20
<212> TYPE: DNA
<213> ORGANISM: Artificial sequence
<220> FEATURE:
<223> OTHER INFORMATION: Amplification primer

<400> SEQUENCE: 55
aaccctctac ccacctaaat                                             20

<210> SEQ ID NO 56
<211> LENGTH: 20
<212> TYPE: DNA
<213> ORGANISM: Artificial sequence
<220> FEATURE:
<223> OTHER INFORMATION: Amplification primer

<400> SEQUENCE: 56
tttagttgag ggaaggggaa                                             20

<210> SEQ ID NO 57
<211> LENGTH: 22
<212> TYPE: DNA
<213> ORGANISM: Artificial sequence
<220> FEATURE:
<223> OTHER INFORMATION: Amplification primer

<400> SEQUENCE: 57
aactacaaca caactacct aa                                           22

<210> SEQ ID NO 58
<211> LENGTH: 25
<212> TYPE: DNA
<213> ORGANISM: Artificial sequence
<220> FEATURE:
<223> OTHER INFORMATION: Amplification primer

<400> SEQUENCE: 58
tgttgtgtat aattattttg agggt                                       25

<210> SEQ ID NO 59
<211> LENGTH: 24
<212> TYPE: DNA
<213> ORGANISM: Artificial sequence
<220> FEATURE:
<223> OTHER INFORMATION: Amplification primer

<400> SEQUENCE: 59
ccaatctaac cataaaccta caca                                        24

<210> SEQ ID NO 60
<211> LENGTH: 28
<212> TYPE: DNA
<213> ORGANISM: Artificial sequence
<220> FEATURE:
<223> OTHER INFORMATION: Amplification primer

```
<400> SEQUENCE: 60
caacaaccac aacattaaac tcataaac                                        28

<210> SEQ ID NO 61
<211> LENGTH: 23
<212> TYPE: DNA
<213> ORGANISM: Artificial sequence
<220> FEATURE:
<223> OTHER INFORMATION: Amplification primer

<400> SEQUENCE: 61
cgtcgtgtat aattatttcg agg                                             23

<210> SEQ ID NO 62
<211> LENGTH: 22
<212> TYPE: DNA
<213> ORGANISM: Artificial sequence
<220> FEATURE:
<223> OTHER INFORMATION: Amplification primer

<400> SEQUENCE: 62
gatctaaccg taaacctacg cg                                              22

<210> SEQ ID NO 63
<211> LENGTH: 24
<212> TYPE: DNA
<213> ORGANISM: Artificial sequence
<220> FEATURE:
<223> OTHER INFORMATION: Amplification primer

<400> SEQUENCE: 63
cgacgaccgc gacgttaaac tcgt                                            24

<210> SEQ ID NO 64
<211> LENGTH: 23
<212> TYPE: DNA
<213> ORGANISM: Artificial sequence
<220> FEATURE:
<223> OTHER INFORMATION: Amplification primer

<400> SEQUENCE: 64
taaatacaaa ccaaaacact ccc                                             23

<210> SEQ ID NO 65
<211> LENGTH: 24
<212> TYPE: DNA
<213> ORGANISM: Artificial sequence
<220> FEATURE:
<223> OTHER INFORMATION: Amplification primer

<400> SEQUENCE: 65
gttatatgtt ggttatgtgt gttt                                            24

<210> SEQ ID NO 66
<211> LENGTH: 26
<212> TYPE: DNA
<213> ORGANISM: Artificial sequence
<220> FEATURE:
<223> OTHER INFORMATION: Amplification primer

<400> SEQUENCE: 66
ttcccatcaa aaacccacca attaac                                          26

<210> SEQ ID NO 67
<211> LENGTH: 21
```

<212> TYPE: DNA
<213> ORGANISM: Artificial sequence
<220> FEATURE:
<223> OTHER INFORMATION: Amplification primer

<400> SEQUENCE: 67
aatacgaacc aaaacgctcc c                                          21

<210> SEQ ID NO 68
<211> LENGTH: 24
<212> TYPE: DNA
<213> ORGANISM: Artificial sequence
<220> FEATURE:
<223> OTHER INFORMATION: Amplification primer

<400> SEQUENCE: 68
tatgtcggtt acgtgcgttt atat                                       24

<210> SEQ ID NO 69
<211> LENGTH: 22
<212> TYPE: DNA
<213> ORGANISM: Artificial sequence
<220> FEATURE:
<223> OTHER INFORMATION: Amplification primer

<400> SEQUENCE: 69
cccgtcgaaa acccgccgat ta                                         22

<210> SEQ ID NO 70
<211> LENGTH: 22
<212> TYPE: DNA
<213> ORGANISM: Artificial sequence
<220> FEATURE:
<223> OTHER INFORMATION: Amplification primer

<400> SEQUENCE: 70
tggtaatgga aaagtgtggg aa                                         22

<210> SEQ ID NO 71
<211> LENGTH: 23
<212> TYPE: DNA
<213> ORGANISM: Artificial sequence
<220> FEATURE:
<223> OTHER INFORMATION: Amplification primer

<400> SEQUENCE: 71
cccatccaaa aaatctcaac aaa                                        23

<210> SEQ ID NO 72
<211> LENGTH: 27
<212> TYPE: DNA
<213> ORGANISM: Artificial sequence
<220> FEATURE:
<223> OTHER INFORMATION: Amplification primer

<400> SEQUENCE: 72
ctcacaccac acaatcacaa ttttaat                                    27

<210> SEQ ID NO 73
<211> LENGTH: 21
<212> TYPE: DNA
<213> ORGANISM: Artificial sequence
<220> FEATURE:
<223> OTHER INFORMATION: Amplification primer

<400> SEQUENCE: 73

```
tttcgtggta acggaaaagc g                                              21

<210> SEQ ID NO 74
<211> LENGTH: 22
<212> TYPE: DNA
<213> ORGANISM: Artificial sequence
<220> FEATURE:
<223> OTHER INFORMATION: Amplification primer

<400> SEQUENCE: 74
ccgtccaaaa aatctcaacg aa                                             22

<210> SEQ ID NO 75
<211> LENGTH: 23
<212> TYPE: DNA
<213> ORGANISM: Artificial sequence
<220> FEATURE:
<223> OTHER INFORMATION: Amplification primer

<400> SEQUENCE: 75
ctcacgccgc gcaatcgcaa ttt                                            23

<210> SEQ ID NO 76
<211> LENGTH: 22
<212> TYPE: DNA
<213> ORGANISM: Artificial sequence
<220> FEATURE:
<223> OTHER INFORMATION: Amplification primer

<400> SEQUENCE: 76
atttttgggt ggtgtgtgtg tt                                             22

<210> SEQ ID NO 77
<211> LENGTH: 22
<212> TYPE: DNA
<213> ORGANISM: Artificial sequence
<220> FEATURE:
<223> OTHER INFORMATION: Amplification primer

<400> SEQUENCE: 77
tcaaaaactc acaccacaaa cc                                             22

<210> SEQ ID NO 78
<211> LENGTH: 26
<212> TYPE: DNA
<213> ORGANISM: Artificial sequence
<220> FEATURE:
<223> OTHER INFORMATION: Amplification primer

<400> SEQUENCE: 78
aaccacataa caccataaca caacac                                         26

<210> SEQ ID NO 79
<211> LENGTH: 21
<212> TYPE: DNA
<213> ORGANISM: Artificial sequence
<220> FEATURE:
<223> OTHER INFORMATION: Amplification primer

<400> SEQUENCE: 79
tttgattttc gggtggtgcg t                                              21

<210> SEQ ID NO 80
<211> LENGTH: 21
<212> TYPE: DNA
<213> ORGANISM: Artificial sequence
```

```
<220> FEATURE:
<223> OTHER INFORMATION: Amplification primer

<400> SEQUENCE: 80
tcaaaaactc gcgccacaaa c                                              21

<210> SEQ ID NO 81
<211> LENGTH: 23
<212> TYPE: DNA
<213> ORGANISM: Artificial sequence
<220> FEATURE:
<223> OTHER INFORMATION: Amplification primer

<400> SEQUENCE: 81
aaccacgtaa cgccgtaacg cga                                            23

<210> SEQ ID NO 82
<211> LENGTH: 24
<212> TYPE: DNA
<213> ORGANISM: Artificial sequence
<220> FEATURE:
<223> OTHER INFORMATION: Amplification primer

<400> SEQUENCE: 82
ttattagagg gtggggtgga ttgt                                           24

<210> SEQ ID NO 83
<211> LENGTH: 22
<212> TYPE: DNA
<213> ORGANISM: Artificial sequence
<220> FEATURE:
<223> OTHER INFORMATION: Amplification primer

<400> SEQUENCE: 83
caaccccaaa ccacaaccat aa                                             22

<210> SEQ ID NO 84
<211> LENGTH: 23
<212> TYPE: DNA
<213> ORGANISM: Artificial sequence
<220> FEATURE:
<223> OTHER INFORMATION: Amplification primer

<400> SEQUENCE: 84
ctactcccca ccacccacta cct                                            23

<210> SEQ ID NO 85
<211> LENGTH: 24
<212> TYPE: DNA
<213> ORGANISM: Artificial sequence
<220> FEATURE:
<223> OTHER INFORMATION: Amplification primer

<400> SEQUENCE: 85
ttattagagg gtggggcgga tcgc                                           24

<210> SEQ ID NO 86
<211> LENGTH: 21
<212> TYPE: DNA
<213> ORGANISM: Artificial sequence
<220> FEATURE:
<223> OTHER INFORMATION: Amplification primer

<400> SEQUENCE: 86
gaccccgaac cgcgaccgta a                                              21
```

<210> SEQ ID NO 87
<211> LENGTH: 23
<212> TYPE: DNA
<213> ORGANISM: Artificial sequence
<220> FEATURE:
<223> OTHER INFORMATION: Amplification primer

<400> SEQUENCE: 87
agtagtatgg agtcggcggc ggg                                          23

<210> SEQ ID NO 88
<211> LENGTH: 21
<212> TYPE: DNA
<213> ORGANISM: Artificial sequence
<220> FEATURE:
<223> OTHER INFORMATION: Amplification primer

<400> SEQUENCE: 88
gggttaggtg gttagggtgt t                                            21

<210> SEQ ID NO 89
<211> LENGTH: 23
<212> TYPE: DNA
<213> ORGANISM: Artificial sequence
<220> FEATURE:
<223> OTHER INFORMATION: Amplification primer

<400> SEQUENCE: 89
taaccaaaca cctccatcat atc                                          23

<210> SEQ ID NO 90
<211> LENGTH: 28
<212> TYPE: DNA
<213> ORGANISM: Artificial sequence
<220> FEATURE:
<223> OTHER INFORMATION: Amplification primer

<400> SEQUENCE: 90
aaacacacac caaccaaata aaaaccat                                     28

<210> SEQ ID NO 91
<211> LENGTH: 20
<212> TYPE: DNA
<213> ORGANISM: Artificial sequence
<220> FEATURE:
<223> OTHER INFORMATION: Amplification primer

<400> SEQUENCE: 91
ggttaggcgg ttagggcgtc                                              20

<210> SEQ ID NO 92
<211> LENGTH: 20
<212> TYPE: DNA
<213> ORGANISM: Artificial sequence
<220> FEATURE:
<223> OTHER INFORMATION: Amplification primer

<400> SEQUENCE: 92
ccgaacgcct ccatcgtatc                                              20

<210> SEQ ID NO 93
<211> LENGTH: 25
<212> TYPE: DNA
<213> ORGANISM: Artificial sequence
<220> FEATURE:
<223> OTHER INFORMATION: Amplification primer

```
<400> SEQUENCE: 93
cacacaccga ccgaataaaa accgt                                          25
```

QUANTITATIVE MULTIPLEX METHYLATION-SPECIFIC PCR

CROSS REFERENCE TO RELATED APPLICATION(S)

This application is a continuation application of U.S. application Ser. No. 10/976,932, filed Oct. 28, 2004, now U.S. Pat. No. 8,062,849 which claims the benefit of priority under 35 U.S.C. §119(e) of U.S. Ser. No. 60/515,100, filed Oct. 28, 2003, the entire contents of which are incorporated herein by reference.

GRANT INFORMATION

This invention was made with Government support under DAMD 17-01-1-0286, awarded by the Department of Defense, and the NIH P50CA88843 awarded by the National Cancer Institute. The government has certain rights in the invention.

BACKGROUND OF THE INVENTION

1. Field of the Invention

The invention relates generally to cancer markers and more specifically to a method of evaluating gene methylation within a sample, referred to herein as quantitative multiplex methylation-specific PCR (QM-MSP), in order to detect conditions associated with methylation status of genes.

2. Background Information

Epigenetic alterations including hypermethylation of gene promoters are proving to be consistent and early events in neoplastic progression (Hanahan D. and Weinberg R. A. *Cell* (2000) 100:57-70; Warnecke P. M. and Bestor T. H. *Cum Opin Oncol* (2000) 12:68-73; Yang X. et al. *Endocr Relat Cancer* (2001) 8:115-127; and Widschwendter M. and Jones P. A. *Oncogene* (2002) 211:5462-5482). Such alterations are thought to contribute to the neoplastic process by transcriptional silencing of tumor suppressor gene expression, and by increasing the rate of genetic mutation (Wajed S. A. et al. *Ann Surg* (2001) 234:10-20 and Jones P. A. and Baylin S. B. *Nat Rev Genet* (2002) 3: 415-428). DNA methylation is reversible, since it does not alter the DNA sequence; however, it is heritable from cell to cell. Methylated genes can serve as biomarkers for early detection of cancer for risk assessment and for predicting response to therapy.

Widschwendter and Jones (supra) reviewed over 40 genes whose expression is lost in breast cancer due to promoter hypermethylation, and others have studied hypermethylation of genes including NES-1 (Goyal J. et al. *Cancer Res* (1998) 58:4782-4786; Dhar S. et al. *Clin Cancer Res* (2001) 7:3393-3398; Li B. et al. *Cancer Res* (2001) 61:8014-8021; and Yunes M. J. et al. *Int J Radiat Oncol Biol Phys* (2003) 56:653-657) APC (Kashiwaba M. et al. *J Cancer Res Clin Oncol* (1994) 120:727-731; Virmani A. K. et al. *Clin Cancer Res* (2001) 7:1998-2004; and Sarrio D. et al. *Int J Cancer* (2003) 106:208-215), Cyclin D2 (Evron E. et al. *Cancer Res* (2001) 61:2782-2787 and Lehmann U. et al. *Am J Pathol* (2002) 160:605-612), RARB (Widschwendter M. et al. *J Natl Cancer Inst* (2000) 92:826-832; Yan L. et al. *J Mammary Gland Biol Neoplasia* (2001) 6:183-192; and Sirchia S. M. et al. *Cancer Res* (2002) 62: 2455-2461), TWIST (Evron E. et al. *Lancet* (2001) 357:1335-1336), RASSF1A (Lehmann U. et al. *Cancer Res* (2001) 61:8014-8021; Burbee D. G. et al. *J Natl Cancer Inst* (2001) 93:691-699; and Dammann R. et al. *Cancer Res* (2001) 61:3105-3109), and HIN1 (Krop I. E. et al. *Proc Natl Acad Sci USA* (2001) 98:9796-9801) in tissue, blood and ductal fluids. Since methylation changes often appear early in disease, detection of hypermethylated genes could identify tissues derived from subjects with increased risk. Furthermore, the reversible nature of methylation offers the potential to revert aspects of the cancer phenotype with the appropriate therapy (Fackler M. J. et al. *J Mammary Gland Biol Neoplasia* (2003) 8:75-89).

Tumor DNA can be found in various body fluids and these fluids can potentially serve as diagnostic material. Evaluation of tumor DNA in these fluids requires methods that are specific as well as sensitive. For instance, a PCR-base technique called methylation-specific PCR (MSP) is reported to detect one copy of methylated genomic DNA in one-thousand unmethylated copies of genomic DNA (Herman J. G. et al. *Proc Natl Acad Sci USA* (1996) 93:9821-9826). This approach has been modified in order to co-amplify several genes simultaneously in a nested or multiplex MSP assay (Palmisano W. A. et al. *Cancer Res* (2000) 60:5954-5958; Buller A. et al. *Mol Diagn* (2000) 5:239-243; and Brock M. V. et al. *Clin Cancer Res* (2003) 9:2912-2919). The read out is gel-based and qualitative ("all or nothing"). This method has been used to establish the frequency of gene promoter hypermethylation among subjects with bronchial and esophageal carcinoma. However, the method cannot quantitatively measure the levels of gene methylation.

Quantitative real time PCR (Q-PCR) allows a highly sensitive quantification of transcriptional levels or levels of the DNA of the gene of interest in a few hours with minimal handling the samples (Heid C. A. et al. *Genome Res* (1996) 6:986-994 and Gibson U. E. et al. *Genome Res* (1996) 6:995-1001). cDNA or genomic copies of the gene of interest are quantitated by detecting PCR products as they accumulate using an optically detectable polynucleotide probe. This technique is widely used.

Quantitative MSP (Q-MSP) allows highly sensitive detection of gene promoter methylation levels by real time PCR with methylation-specific primers probes (Lo Y. M. et al. *Cancer Res* (1999) 59:3899-3903; Trinh B. N. *Methods* (2001) 25:456-462; Wong I. H. et al. *Clin Cancer Res* (2003) 9:1047-1052).

The advantage of fluorogenic probes over DNA binding dyes (e.g. syber green for real time PCR) is that specific hybridization between probe and target is required to generate fluorescent signal. Thus, with fluorogenic probes, non-specific amplification due to mis-priming or primer-dimer artifact does not generate signal. However, Q-MSP analysis of multiple genes requires additional quantities of template DNA. Therefore, new and better methods are needed to increase the amount of available DNA and to quantitate detection of gene methylation status for several genes.

SUMMARY OF THE INVENTION

The invention is based on the discovery of a method for evaluating the degree of gene methylation within a single DNA sample, referred to herein as quantitative multiplex methylation-specific PCR (QM-MSP), to co-amplify many genes from amounts of sample previously used for just one or two genes. The invention provides a basis to define the extent of gene promoter hypermethylation across a panel of genes, enhancing the discriminatory power of this test to distinguish between normal and altered condition(s). Determination of hypermethylation as compared with normal methylation of samples may help to stratify different types or stages of conditions, such as cancer, associated with gene hypermethylation. The QM-MSP method is based on real-time PCR that uses one or more distinguishable optically detectable probes to increase the assay specificity and the sensitivity such that one to ten copies of the desired methylated gene among 100,000 unmethylated copies of the gene can be detected (Fackler M. J. et al. *Cancer Res* (2004) 64:4442-4452). QM-MSP is more economical in time and materials, is more informative, quantitative, and suitable for clinical format than MSP, multiplex MSP or Q-MSP. The invention methods solve the dilemma of how best to distribute the available DNA to allow robust quantitative analyses of many different genes from precious small samples.

In one embodiment, the invention provides methods for determining the methylation status of DNA in a sample by co-amplifying a plurality of DNA sequences using a mixture of DNA sequence-specific, methylation status-independent outer primer pairs that selectively hybridize to their cognate DNA sequences under conditions that allow generation of a first amplification product containing first amplicons. Real time PCR is then used to amplify unmethylated and/or methylated DNA from the first amplicons under conditions that allow generation of second amplification products for one or more genes, using two sets of primers comprising a DNA sequence-specific, methylation status-dependent (unmethylated or methylated) inner primer pair and a (unmethylated or methylated) DNA sequence-specific probe. Second amplicons are detected by using one or more distinguishable optically detectable labels per reaction. A combination of inner primer pair and probe selectively hybridizes to one first amplicon, and the sets of inner primer pairs and probes collectively hybridize to a plurality of first amplicons in the first amplification product. Signal intensities of the one or more distinguishable labels in the second amplification products are detected to determine the amount of methylation in a gene. A combined methylation value is derived for the methylation in the DNA sequences in the test sample from amounts of methylation determined for the second amplification products across a panel of genes. For the purposes of determining whether the gene amplicon is hyper- or hypo-methylated, the combined methylation value of the test sample is compared with the combined methylation value in a series of comparable normal DNA samples.

In yet another embodiment, the invention provides methods of diagnosing development of a condition associated with aberrant methylation of DNA in tissue of a subject by co-amplifying a plurality of DNA sequences using a mixture of DNA sequence-specific, methylation status-independent outer primer pairs that selectively hybridize to their cognate DNA sequences under conditions that allow generation of a first amplification product containing first amplicons. Real time PCR is then used to amplify unmethylated and/or methylated DNA from the first amplicons under conditions that allow generation of second amplification products for one or more genes, using for a gene two sets primers comprising a DNA sequence-specific, methylation status-dependent (unmethylated or methylated) inner primer pair and a (unmethylated or methylated) DNA sequence-specific probe. Second amplicons are detected by using one or more distinguishable optically detectable labels per reaction. A combination of inner primer pair and probe selectively hybridizes to one first amplicon, and the sets of inner primer pairs and probes collectively hybridize to a plurality of first amplicons in the first amplification product. Signal intensities of the one or more distinguishable labels in the second amplification products are detected to determine the amount of methylation in a gene. A combined methylation value is derived for the methylation in the DNA sequences in the test sample from amounts of methylation determined for the second amplification products across a panel of genes. For the purposes of determining whether the gene amplicon is hyper- or hypo-methylated, the combined methylation value of the tissue of the subject is compared with the combined methylation value in a series of comparable normal DNA samples to diagnose the state of development of the condition in the subject.

In still another embodiment, the invention provides methods for diagnosing development of a cancer associated with hypermethylation of CpG island DNA in carcinoma-associated tissue of a subject by co-amplifying CpG islands in a subject sample comprising several different DNA sequences isolated from the carcinoma-associated tissue using a mixture of DNA sequence-specific, methylation status-independent outer primer pairs that selectively hybridize to one or more of the DNA sequences under conditions that allow generation of a first amplification product containing first amplicons. Then, real time PCR is used to co-amplify the CpG islands in the first amplicons under conditions that allow generation of one or more second amplification products, using one or more members of a set of DNA sequence-specific probes comprising distinguishable fluorescent moieties and one or more members of a set of DNA sequence-specific methylation status-dependent inner primer pairs that selectively hybridize to one or more first amplicon, wherein the sets of probes and inner primer pairs collectively hybridize to a plurality of different first amplicons in the first amplification product. Fluorescence due to the presence of distinguishable fluorescent moieties in the second amplification products are detected to determine the amount of methylation of the CpG islands therein; and a combined methylation value for the methylation in the tissue of the subject is derived from the amounts of methylation determined for the second amplification products as compared with a combined methylation value in comparable normal tissue to diagnose the state of development of the cancer in the subject.

In yet another embodiment, the invention provides methods for diagnosing the state of development of a condition associated with hypermethylation of a gene in a mammalian subject by co-amplifying a plurality of different DNA sequences isolated from tissue of the subject associated with the condition using a mixture of DNA sequence-specific, methylation status-independent outer primer pairs that selectively hybridize to one or more of the DNA sequences under conditions that allow generation of a first amplification product containing first amplicons. Real time PCR is then used to co-amplify the first amplicons under conditions that allow generation of one or more second amplification products using one or more members of a set of DNA sequence-specific probes comprising distinguishable optically detectable labels and one or more members of a set of DNA sequence-specific methylation status-dependent inner primer pairs that selectively hybridize to a cognate first amplicon, wherein the sets of probes and inner primer pairs collectively amplify a plurality of different first amplicons in the first amplification product. Signal intensity of the distinguishable labels in the second amplification products is detected to determine the amount of methylation of the second amplification products. A combined methylation value is derived for the methylation in the DNA sequences from amounts of methylation determined for the second amplification products in the DNA of the subject as compared with the combined methylation value in a comparable normal DNA sample to indicate the state of development of the condition in the subject.

In another embodiment, the invention provides kits for determining the methylation status of a plurality of DNA sequences in a DNA sample. The invention kits include a set of DNA sequence-specific, methylation status-independent outer primer pairs that selectively hybridize to cognate DNA sequences under conditions that allow generation of a first amplification product containing first amplicons; a set of DNA sequence-specific, methylation status-dependent inner primer pairs; and a set of DNA sequence-specific probes with one or more distinguishable optically detectable labels. A combination of inner primer pair and probe selectively hybridizes to one or more first amplicon, and the sets of inner primer pairs and probes collectively hybridize to a plurality of first amplicons in the first amplification product.

BRIEF DESCRIPTION OF THE FIGURES

FIG. 1A is a schematic representation of the protocol for quantitative multiplex methylation-specific PCR (QM-MSP) as used in the invention methods. In reaction #1 (RXN 1) a cocktail of gene-specific primer pairs is used to co-amplify DNA for a plurality of genes independent of their DNA methylation status. In reaction #2 (RXN 2) quantitative real-time PCR is performed with gene-specific primers using the DNA template derived from RXN 1 (diluted between 1:5 to 1:10$^4$). Unmethylated (U) and methylated (M) DNA were quantitated separately using methylation-status specific primers and a probe conjugated with the 6FAM label and TAMRA quencher. The probe is progressively degraded with each cycle of PCR and the fluorescence signal generated by FAM is directly proportional to the extent of DNA amplification. To perform methylation analyses on two genes simultaneously, RXN 2 also can contain a second set of gene-specific internal methylation-dependent primers in combination with a probe conjugated with a different label, such as VIC™, as indicated by the schematic and amplification plots for U RASSF1A and U RARβ (FIG. 1B).

FIG. 2A shows a plot of $\Delta C_T$ ($\Delta C_T = C_T M - C_T U$) versus dilution. FIG. 2B shows standard curve plots ($C_T$ vs Quantity) of serially diluted DNA. A slope of −3.33 reflects a 2-fold amplification of DNA per cycle. The correlation coefficient (R2) shows linearity (0.999) over the range of DNA concentrations.

FIGS. 3A-B are graphs showing PCR cycles (X axis) plotted against the fluorescence intensity of the probe (Y axis) for multiplexed human sperm DNA (HSD) (FIG. 3B) or MDA-MB231 (FIG. 3A) template tested with unmethylated (U) and methylated (M) primers for RASSF1A. The unmethylated and methylated reactions were 100% specific since U primers did not cross-react with MDA-MB231 DNA (100% methylated) and M primers did not cross-react with HSD (100% unmethylated) DNA.

FIG. 4B: 60 ng HSD DNA and 40 pg 231 DNA) were subjected to QM-MSP.

FIG. 6A represents cumulative methylation in normal mammoplasty and tumor in a subgroup of samples from FIG. 5 where results were available for all four genes in the panel, normal (Mam; n=9) and tumor (n=19) were scored for cumulative methylation by adding the % M for all four genes within each sample. A maximum of 400 relative methylation units was possible (e.g. MDA-MB231 control DNA is 100% methylated for each of the four genes). The bar height reflects total cumulative methylation, while the segments correspond to the relative amounts of methylation of each gene indicated. FIG. 6B shows mean cumulative methylation in normal mammoplasty versus tumor as determined by the unpaired t test (untransformed p=0.0002; transformed p=0.0001). Plotted is the mean (±standard error of the mean) amount of cumulative methylation.

FIG. 7A shows the cumulative methylation in paired samples of adjacent normal and tumor tissue (n=6) as quantitated by QM-MSP. Total possible units=400 (4 genes×100%). The mean of normal mammoplasty (n=9) samples (Mam) from FIG. 6B is shown at left. FIG. 7B shows mean cumulative methylation in adjacent normal versus tumor (compared to normal mammoplasty). Differences between normal mammoplasty samples (median=0) and adjacent normal tissue samples (median=9 units) were significant (p=0.01; based on the Mann-Whitney test). Plotted is the mean (±standard error of the mean) amount of cumulative methylation found above in adjacent normal tissues (mean 11.7±4.07) and the nearby tumor (mean 129±39.9), compared to normal mammoplasty (FIG. 7B) (mean 2.61±2.05; as shown in FIG. 6B). The percentage of methylation by gene as well as the extent of cumulative methylation is indicated in the table (FIG. 7C) below the bar graphs.

Figure 11A:
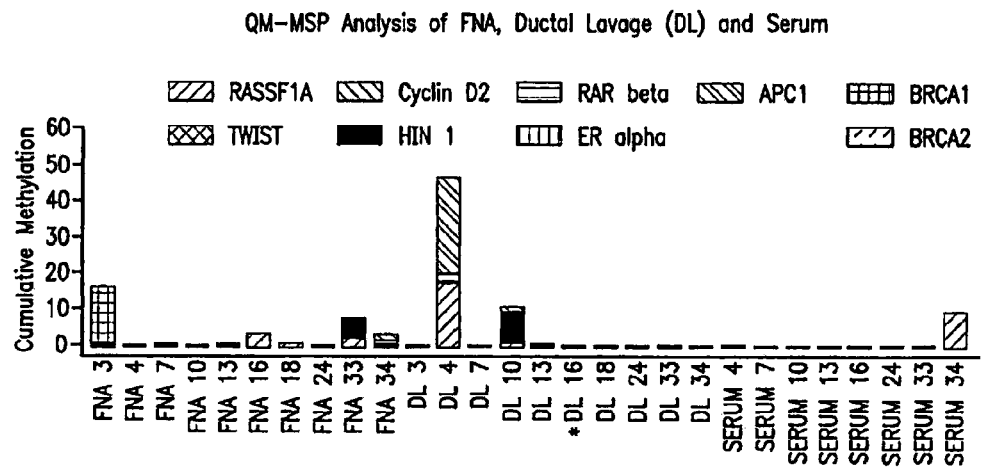
Figure 11B:
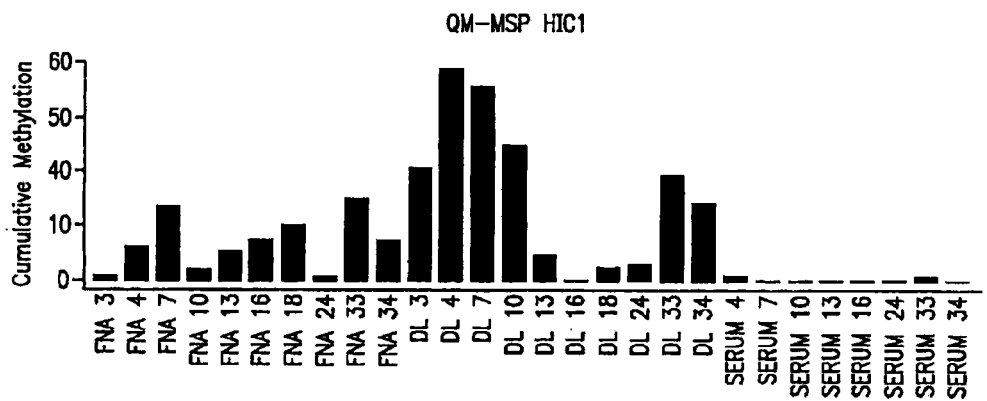

FIGS. 11A-B show the level of gene promoter hypermethylation in DNA from a series of patients (n=10) at high risk of developing breast cancer, but who are not know to have cancer. Paired samples of DNA isolated from serum and from cells obtained by fine needle aspiration (FNA) and ductal lavage (DL) (50-1000 cells) of each patient were analyzed by QM-MSP. FIG. 11A shows the cumulative methylation of RARβ, RASSF1A, TWIST, Cyclin D2, HIN1, ESR1, APC1, BRCA1 and BRCA2 genes. The relative level of methylation of each gene is indicated by the height of the bar. Total possible units=900 (9 genes×100%). FIG. 11B shows the percentage of methylation of HIC1 determined by QM-MSP in the patient samples. Gene promoter hypermethylation of HIC1 was found to be significantly higher in FNA and DL samples than for other genes within the panel. For this reason, HIC1 was analyzed separately from the other genes rather than include HIC1 in the cumulative total for each patient.

Figure 12:
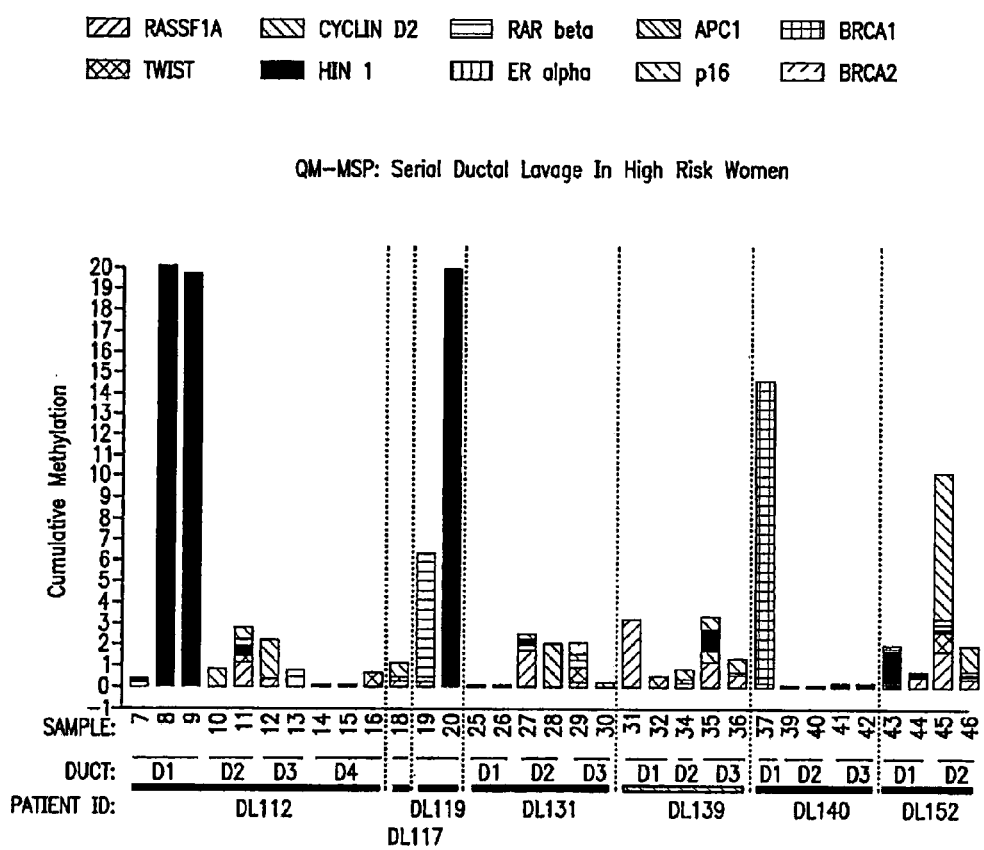

FIG. 12 is a bar graph showing the level of gene promoter hypermethylation in cells derived from ductal lavage fluid from a series of patients (n=7) at high risk of developing breast cancer, but who are not know to have cancer. In most individuals, ducts (D1-D4) from both breasts were serially sampled at 6-9 month intervals (left to right, respectively). Shown is the cumulative methylation of RARβ, RASSF1A, TWIST, Cyclin D2, H1N1, ESR1, APC1, BRCA1, BRCA2, and p16 (CDKN2A) genes within the DNA sample. The relative level of methylation of each gene is indicated by the height of the bar. Total possible units=1000 (10 genes× 100%).

Figure 13A:
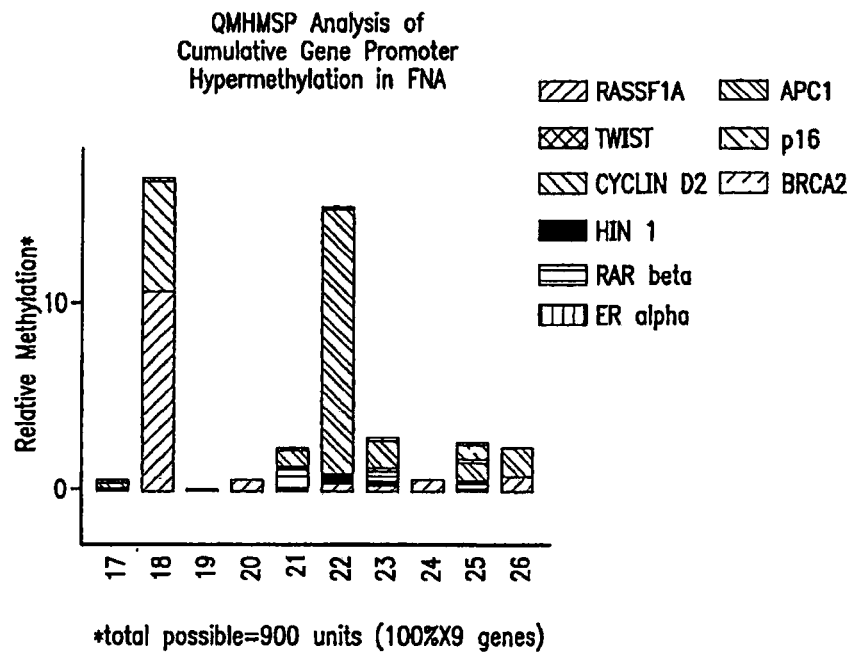
Figure 13B:
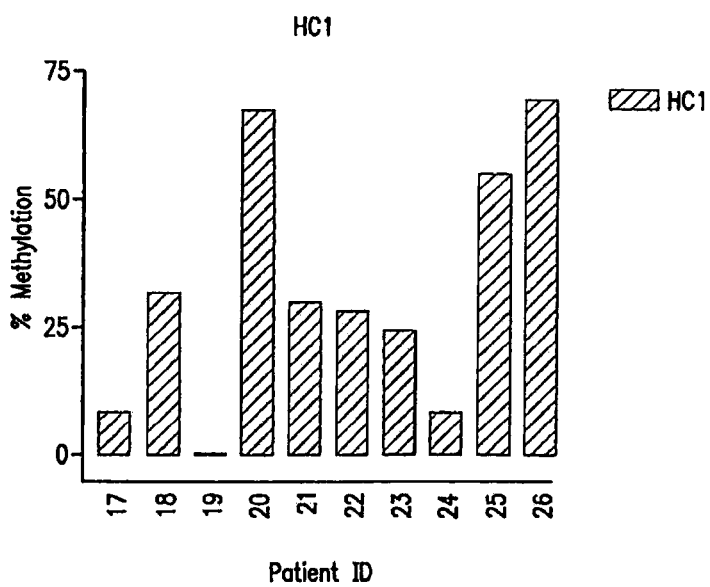

FIGS. 13A-B are bar graphs showing the level of gene promoter hypermethylation in cells derived from nipple aspiration fluid (n=10) from a series of patients (n=7) at high risk of developing breast cancer, but who are not know to have cancer. FIG. 13A shows the cumulative methylation of RARβ, RASSF1A, TWIST, Cyclin D2, HIN1, ESR1, APC1, BRCA1, and BRCA2 genes within the DNA sample. The relative level of methylation of each gene is indicated by the height of the bar. Total possible units=900 (9 genes×100%). FIG. 13B shows high levels of HIC1 methylation were discovered these cytologically benign samples, as indicated by the bar graph showing % methylation within each sample.

DETAILED DESCRIPTION OF THE INVENTION

In the invention methods employing a two-step quantitative multiplex-methylation specific PCR (QM-MSP), many genes can be co-amplified from amounts of sample previously used for just one gene and a combined methylation score can be generated for the panel of genes. The QM-MSP technique combines the sensitivity of multiplex PCR with the quantitative features of quantitative methylation-specific PCR (Q-MSP) in such a way that a panel of genes whose hypermethylation is associated with a type of carcinoma can be co-amplified from limiting amounts of DNA derived from tissue or samples sources of the subject being tested. The invention methods also provide quantitative definition of the extent of gene hypermethylation in normal appearing tissues on a gene-by-gene basis. Thus, the invention methods may be used to more powerfully discriminate between normal or benign tissues and malignant tissues and to monitor or assess the course of cancer development in a subject.

The invention methods are also broadly applicable to evaluation of any of hundreds of genes from hypermethylated regions of genomic DNA derived from but not limited to human or non-human mammals, plants and insects. For example in mammals, such as humans, samples may be derived from different tissue sources and bodily fluids, including one or more selected from tumor-associated tissue, normal tissue, blood, serum, plasma, ductal lavage fluid, nipple aspiration fluid, lymph, duct cells, lymph nodes, and bone marrow of the subject being tested. In mammals, conditions associated with aberrant methylation of genes that can be detected or monitored include, but are not limited to, carcinomas and sarcomas of all kinds, including one or more specific types of cancer, e.g., breast cancer, an alimentary or gastrointestinal tract cancer such as colon, esophageal and pancreatic cancer, a liver cancer, a skin cancer, an ovarian cancer, an endometrial cancer, a prostate cancer, a lymphoma, hematopoietic tumors, such as a leukemia, a kidney cancer, a lung cancer, a bronchial cancer, a muscle cancer, a bone cancer, a bladder cancer or a brain cancer, such as astrocytoma, anaplastic astrocytoma, glioblastoma, medulloblastoma, and neuroblastoma and their metastases. Suitable pre-malignant lesions to be detected or monitored using the invention include, but are not limited to, lobular carcinoma in situ and ductal carcinoma in situ. The invention methods can be used to assay the DNA of any mammalian subject, including humans, pet (e.g., dogs, cats, ferrets) and farm animals (meat and dairy), and race horses.

Samples obtained from other multicellular organisms, such as insects and plants, may also be evaluated for gene methylation status using the invention methods. For example, the methylation status of genes may serve as an indicator of heritability and flexibility of epigenetic states in such subjects. Thus, gene methylation is linked to acquisition of different characteristics in the organism (Frank Lyko *Trends in Gen* (2001) 17:169-172, Finnegan E. J. et al. *Annu Rev Plant Physiol Plant Mol Biol* (1998) 49:223-247).

In one embodiment, the invention provides methods for determining the methylation status of a DNA sample by co-amplifying a plurality of DNA sequences using a mixture of DNA sequence-specific, methylation status-independent outer primer pairs that selectively hybridize to their cognate DNA sequences under conditions that allow generation of a first amplification product containing first amplicons. Real time PCR is then used to amplify unmethylated and/or methylated DNA from the first amplicons under conditions that allow generation of second amplification products for one or more genes, using for a gene two sets of primers comprising a DNA sequence-specific, methylation status-dependent (unmethylated or methylated) inner primer pair and a (unmethylated or methylated) DNA sequence-specific probe. Second amplicons are detected by using one or more distinguishable optically detectable labels per reaction. A combination of inner primer pair and probe selectively hybridizes to one first amplicon, and the sets of inner primer pairs and probes collectively hybridize to a plurality of first amplicons in the first amplification product. Signal intensities of the one or more distinguishable labels in the second amplification products are detected to determine the amount of methylation in a gene. A combined methylation value is derived for the methylation in the DNA sequences in the test sample from amounts of methylation determined for the second amplification products in a panel of genes, as compared with the combined methylation value in comparable normal DNA samples to determine the methylation status of the DNA sample.

In yet another embodiment, the invention provides methods of diagnosing development of a condition such as pregnancy, preeclampsia, or eclampsia associated with aberrant methylation of DNA in tissue of a subject. In this embodiment, the invention methods comprise co-amplifying a plurality of DNA sequences using a mixture of DNA sequence-specific, methylation status-independent outer primer pairs that selectively hybridize to their cognate DNA sequences under conditions that allow generation of a first amplification product containing first amplicons. Real time PCR is then used to amplify unmethylated and/or methylated DNA from the first amplicons under conditions that allow generation of second amplification products for one or more genes, using for a gene two sets of primers, comprising a DNA sequence-specific, methylation status-dependent (unmethylated or methylated) inner primer pair and a (unmethylated or methylated) DNA sequence-specific probe. Second amplicons are detected by using one or more distinguishable optically detectable labels per reaction. A combination of inner primer pair and probe selectively hybridizes to one first amplicon, and the sets of inner primer pairs and probes collectively hybridize to a plurality of first amplicons in the first amplification product. Signal intensities of the one or more distinguishable labels in the second amplification products are detected to determine the amount of methylation in a gene. A combined methylation value is derived for the methylation in the DNA sequences in the test sample from amounts of methylation determined for the second amplification products across a panel of genes as compared with a combined methylation value in comparable normal tissues to diagnose the state of development of the condition in the subject.

In still another embodiment, the invention provides methods for diagnosing development of a carcinoma associated with hypermethylation of CpG island DNA in carcinoma-associated tissue of a subject by co-amplifying CpG islands in a subject sample comprising several different DNA sequences isolated from the carcinoma-associated tissue using a mixture of DNA sequence-specific, methylation status-independent outer primer pairs that selectively hybridize to one or more of the DNA sequences under conditions that allow generation of a first amplification product containing first amplicons. Then, real time PCR is used to co-amplify the CpG islands in the first amplicons under conditions that allow generation of one or more second amplification products, using one or more members of a set of DNA sequence-specific probes comprising distinguishable fluorescent moieties and one or more members of a set of DNA sequence-specific methylation status-dependent inner primer pairs that hybridize to one first amplicon, wherein the sets of probes and inner primer pairs collectively hybridize to a plurality of different first amplicons in the first amplification product. Fluorescence due to the presence of distinguishable fluorescent moieties in the second amplification products is detected to determine the amount of methylation of the CpG islands therein. The combined amount of hypermethylation in CpG islands in the tumor-related tissue compared with a combined amount of methylation in comparable normal tissue is evaluated to diagnose the state of development of the cancer in the subject. For example, the sum of the extent (e.g. percentage) of methylation of the second amplification products across a panel of genes can be used to measure a cumulative amount of hypermethylation in CpG islands in the tumor-related tissue as compared with a cumulative amount of methylation in comparable normal tissue to diagnose the state of development of the carcinoma in the subject.

In yet another embodiment, the invention methods can be used for diagnosing the state of development of a condition, such as any cancer and metastases thereof, associated with hypermethylation or aberrant methylation of a gene in a mammalian subject by co-amplifying a plurality of different DNA sequences isolated from tissue of the subject associated with the condition co-amplifying a plurality of DNA sequences using a mixture of DNA sequence-specific, methylation status-independent outer primer pairs that selectively hybridize to their cognate DNA sequences under conditions that allow generation of a first amplification product containing first amplicons. Real time PCR is then used to amplify unmethylated and/or methylated DNA from the first amplicons under conditions that allow generation of second amplification products for one or more genes, using for a gene two sets of primers comprising a DNA sequence-specific, methylation status-dependent (unmethylated or methylated) inner primer pair and a (unmethylated or methylated) DNA sequence-specific probe. Second amplicons are detected by using one or more distinguishable optically detectable labels per reaction. A combination of inner primer pair and probe selectively hybridizes to one first amplicon, and the sets of inner primer pairs and probes collectively hybridize to a plurality of first amplicons in the first amplification product. Signal intensities of the one or more distinguishable labels in the second amplification products are detected to determine the amount of methylation in a gene. A combined methylation value is derived for the methylation in the DNA sequences in the test sample from amounts of methylation determined for the second amplification products in a panel of genes, as compared with the combined methylation value in comparable normal tissue sample to indicate the state of development of the condition in the subject.

Optionally, in any of the invention methods, a single combination of inner primer pair and probe may be used for amplification using real time PCR in separate aliquots of the first amplification product. In any case, the sets of probes and inner primer pairs collectively amplify a plurality of different first amplicons in the first amplification product.

In another embodiment, the invention provides kits for determining the methylation status of a plurality of DNA sequences in a DNA sample. The invention kits include a set of DNA sequence-specific, methylation status-independent outer primer pairs that selectively hybridize to one or more of the plurality of DNA sequences under conditions that allow generation of a first amplification product containing first amplicons, a set of DNA sequence-specific, methylation status-dependent inner primer pairs, and a set of DNA sequence-specific probes with one or more distinguishable optically detectable labels. A combination of inner primer pair and probe selectively hybridizes to one or more first amplicon, and the sets of inner primer pairs and probes collectively hybridize to a plurality of first amplicons in the first amplification product. The invention kits may include two sets of the set of DNA sequence-specific, methylation status-dependent inner primer pairs, a subset that specifically hybridizes to methylated first amplicons and a subset that specifically hybridizes to unmethylated first amplicons. Illustrative primers are exemplified in the Examples herein. In certain embodiments, the kit may further provide a set of instructions for performing the invention methods using the contents of the kit.

Figure 4A:
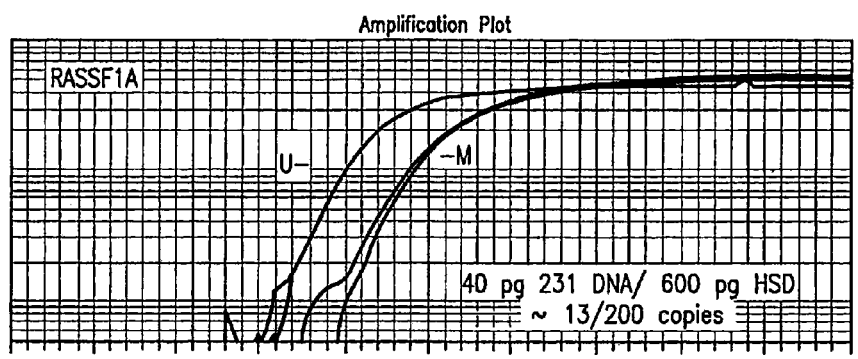
FIGS. 4A-B are graphs showing PCR cycles (X axis) plotted against the fluorescence intensity of the probe (Y axis) indicating detection of hypermethylated genomic RASSF1A DNA in 1500-fold excess of unmethylated DNA. Mixed, bisulfite-treated genomic HSD and 231 DNA (FIG. 4A: 600 pg HSD DNA and 40 pg MDA-MB231 DNA.
Figure 4B:
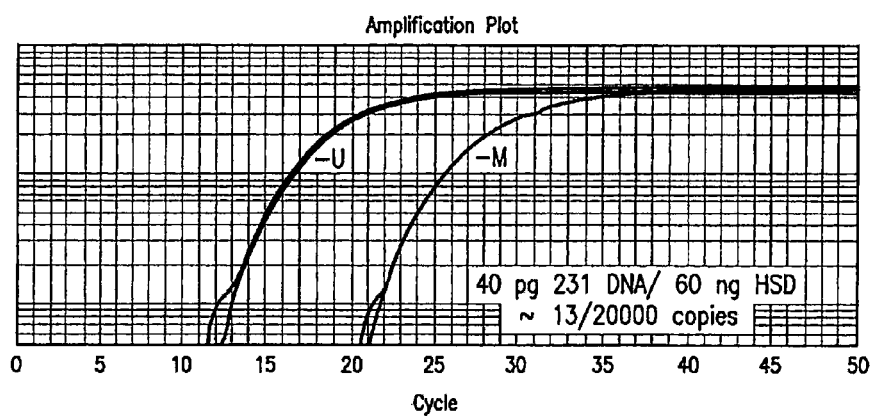

The invention methods combine the principles of MSP, multiplex MSP, quantitative real-time PCR (Q-PCR) with quantitative MSP (Q-MSP) in a procedure referred to herein as quantitative multiplex methylation-specific PCR (QM-MSP) (FIGS. 1 and 2). The studies described herein have shown that this combination of procedures can detect as few as 1-10 methylated copies of DNA in a mixture of about 100,000 copies of unmethylated DNA (Table 3 and FIG. 3) and 40 pg of methylated genomic DNA in up to 1500-fold excess unmethylated DNA (FIG. 4). This outcome compares favorably to Q-MSP with a sensitively of 1:10,000 (Trinh B. N. et al., supra) and conventional MSP with a sensitivity of 1:1000 (Herman J. G. et al., supra). In addition, reactions are specific since no cross-reactivity was observed between methylated and unmethylated primers even in mixtures consisting of more than $10^5$-fold excess of one or the other DNA (Table 3, FIG. 3). Also, it has been demonstrated that using the level of unmethylated product for each gene as the internal control for assessing the extent of methylated gene product present provides accurate quantitation (Table 4).

Quantitative Real-Time PCR (Q-PCR)

The ability to monitor the real-time progress of the PCR changes the way one approaches PCR-based quantification of DNA and RNA. Reactions are characterized by the point in time during cycling when amplification of a PCR product is first detected rather than the amount of PCR product accumulated after a fixed number of cycles. The higher the starting copy number of the nucleic acid target, the sooner a significant increase in fluorescence is observed. FIGS. 3 and 4 show representative amplification plots. An amplification plot is the plot of fluorescence signal versus cycle number. In the initial cycles of PCR, there is little change in fluorescence signal. This defines the baseline for the amplification plot. An increase in fluorescence above the baseline indicates the detection of accumulated PCR product. A fixed fluorescence threshold can be set above the baseline. The parameter $C_T$ (threshold cycle) is defined as the fractional cycle number at which the fluorescence passes the fixed threshold. For example, the PCR cycle number at which fluorescence reaches a threshold value of 10 times the standard deviation of baseline emission may be used as $C_T$ and it is inversely proportional to the starting amount of target cDNA. A plot of the log of initial target copy number for a set of standards versus $C_T$ is a straight line. Quantification of the amount of target in unknown samples is accomplished by measuring $C_T$ and using the standard curve to determine starting copy number.

The entire process of calculating $C_T$s, preparing a standard curve, and determining starting copy number for unknowns can be performed by software, for example that of the 7700 system or 7900 system of Applied Biosystems. Real-time PCR requires an instrumentation platform that consists of a thermal cycler, computer, optics for fluorescence excitation and emission collection, and data acquisition and analysis software. These machines, available from several manufacturers, differ in sample capacity (some are 96-well standard format, others process fewer samples or require specialized glass capillary tubes), method of excitation (some use lasers, others broad spectrum light sources with tunable filters), and overall sensitivity. There are also platform-specific differences in how the software processes data. Real-time PCR machines are available at core facilities or labs that have the need for high throughput quantitative analysis.

Briefly, in the Q-PCR method the number of target gene copies can be extrapolated from a standard curve equation using the absolute quantitation method. For each gene, cDNA from a positive control is first generated from RNA by the reverse transcription reaction. Using about 1 μl of this cDNA, the gene under investigation is amplified using the primers by means of a standard PCR reaction. The amount of amplicon obtained is then quantified by spectrophotometry and the number of copies calculated on the basis of the molecular weight of each individual gene amplicon. Serial dilutions of this amplicon are tested with the Q-PCR assay to generate the gene specific standard curve. Optimal standard curves are based on PCR amplification efficiency from 90 to 100% (100% meaning that the amount of template is doubled after each cycle), as demonstrated by the slope of the standard curve equation. Linear regression analysis of all standard curves should show a high correlation ($R^2$ coefficient≥0.98). Genomic DNA can be similarly quantified.

When measuring transcripts of a target gene, the starting material, transcripts of a housekeeping gene are quantified as an endogenous control. Beta-actin is one of the most used nonspecific housekeeping genes. For each experimental sample, the value of both the target and the housekeeping gene are extrapolated from the respective standard curve. The target value is then divided by the endogenous reference value to obtain a normalized target value independent of the amount of starting material.

Primer and Probe Design for QM-MSP

In practice of the invention methods, the above-described quantitative real-time PCR methodology has been adapted to perform quantitative methylation-specific PCR (QM-MSP) by utilizing the external primers pairs in round one (multiplex) PCR and internal primer pairs in round two (real time MSP) PCR. Thus each set of genes has one pair of external primers and two sets of three internal primers/probe (internal sets are specific for unmethylated or methylated DNA). The external primer pairs can co-amplify a cocktail of genes, each pair selectively hybridizing to a member of the panel of genes being investigated using the invention method. Primer pairs are designed to exclude CG dinucleotides, thereby rendering DNA amplification independent of the methylation status of the promoter DNA sequence. Therefore methylated and unmethylated DNA sequences internal to the binding sites of the external primers are co-amplified for any given gene by a single set of external primers specific for that gene. The external primer pair for a gene being investigated is complementary to the sequences flanking the CpG island that is to be queried in the second round of QM-MSP. For example, the sequences of external primers set forth in Table 1 below are used for multiplex PCR (first round PCR) of genes associated with primary breast cancer (Fackler M. J. et al, *Int. J. Cancer* (2003) 107:970-975; Fackler M. J. et al. *Cancer Res* (2004) 64:4442-4452).

Internal PCR primers used for quantitative real-time PCR of methylated and unmethylated DNA sequences (round two QM-MSP) are designed to selectively hybridize to the first amplicon produced by the first round of PCR for one or more members of the panel of DNA sequences being investigated using the invention method and to detect the methylation status, i.e., whether methylated (M) or unmethylated (U), of the CpG islands in the first amplicons to which they bind. Thus for each member of the starting panel of promoter DNA sequences used in an invention assay, separate QM-MSP reactions are conducted to amplify the first amplicon produced in the first round of PCR using the respective methylation-specific primer pair and using the respective unmethylated-specific primer pair.

In round two of QM-MSP a single gene or a cocktail of two or more genes can be co-amplified using distinguishable fluorescence labeled probes. The probes used in the round two QM-MSP of the invention method are designed to selectively hybridize to a segment of the first amplicon lying between the binding sites of the respective methylation-status specific internal PCR primer pair. Polynucleotide probes suitable for use in real-time PCR include, but are not limited to, a bilabeled oligonucleotide probe, such as a molecular beacon or a TaqMan™ probe, which include a fluorescent moiety and a quencher moiety. In a molecular beacon the fluorescence is generated due to hybridization of the probe, which displaces the quencher moiety from proximity of the fluorescent moiety due to disruption of a stem-loop structure of the bilabeled oligonucleotide. Molecular beacons, such as Amplifluor™ or TriStar™ reagents and methods are commercially available (Stratagene; Intergen). In a TaqMan™ probe, the fluorescence is progressively generated due to progressive degradation of the probe by Taq DNA polymerase during rounds of amplification, which displaces the quencher moiety from the fluorescent moiety. Once amplification occurs, the probe is degraded by the 5'-3' exonuclease activity of the Taq DNA polymerase, and the fluorescence can be detected, for example by means of a laser integrated in the sequence detector. The fluorescence intensity, therefore, is proportional to the amount of amplification product produced.

In one embodiment, fluorescence from the probe is detected and measured during a linear amplification reaction and, therefore, can be used to detect generation of the linear amplification product.

Amplicons in the 80-150 base pair range are generally favored because they promote high-efficiency assays that work the first time. In addition, high efficiency assays enable quantitation to be performed using the absolute quantitation method. Quantitation of the copy number of unmethylated (U) and methylated (M) DNA amplicons for a specific gene eliminates the need to use actin as an estimate of DNA input, since U+M is taken to approximate the total number of copies of DNA amplicons for any given gene in the first amplicon product (derived from round one, multiplex PCR of QM-MSP).

Whenever possible, primers and probes can be selected in a region with a G/C content of 20-80%. Regions with G/C content in excess of this may not denature well during thermal cycling, leading to a less efficient reaction. In addition, G/C-rich sequences are susceptible to non-specific interactions that may reduce reaction efficiency. For this reason, primer and probe sequences containing runs of four or more G bases are generally avoided. A/T-rich sequences require longer primer and probe sequences in order to obtain the recommended TMs. This is rarely a problem for quantitative assays; however, TaqMan™ probes approaching 40 base pairs can exhibit less efficient quenching and produce lower synthesis yields.

For example, external primer pairs, internal primer pairs and gene-specific probes for determining the methylation and unmethylation status of certain genes associated with primary breast cancer, RASSF1A, TWIST, Cyclin D2, and HIN1, are set forth in Tables 1 and 2 below.

TABLE 1

Sequence of Multiplex External Primers (Used in Round 1 PCR of QM-MSP)

| Primer Name | Primer Sequence | Orientation | SEQ ID NO. |
|---|---|---|---|
| Cyclin D2 Ext F | Tattttttgtaaagatagttttgat | Forward | SEQ ID NO: 1 |
| Cyclin D2 Ext R | Tacaactttctaaaaaataaccc | Reverse | SEQ ID NO: 2 |
| RASSF1A Ext F(2) | Gttttatagttttgtatttagg | Forward | SEQ ID NO: 3 |
| RASSF1A Ext R(2) | Aactcaataaactcaaactccc | Reverse | SEQ ID NO: 4 |
| TWIST Ext R(4) | Cctcccaaaccattcaaaaac | Forward | SEQ ID NO: 5 |
| TWIST Ext F(3) | Gagatgagatattatttattgtg | Reverse | SEQ ID NO: 6 |
| RARB Ext F | Gtaggagggtttatttttttgtt | Forward | SEQ ID NO: 7 |
| RARB Ext R(2) | Aattacattttccaaacttactc | Reverse | SEQ ID NO: 8 |
| HIN1 Ext F(2) | Gttttgttaagaggaagtttt | Forward | SEQ ID NO: 9 |
| HIN1 Ext R | Ccgaaacatacaaaacaaaaccac | Reverse | SEQ ID NO: 10 |
| ACTB Ext F | Tatataggttggggaagtttg | Forward | SEQ ID NO: 11 |
| ACTB Ext R | Tataaaaacataaaacctataacc | Reverse | SEQ ID NO: 12 |
| ESR1 Ext F(2) | Ggtgtatttggatagtagtaag | Forward | SEQ ID NO: 46 |
| ESR1 Ext R(3) | Ctccaaataataaaacacctact | Reverse | SEQ ID NO: 47 |
| APC1 Ext F(2) | Aaaaccctataccccactac | Forward | SEQ ID NO: 48 |
| APC1 Ext R(2) | Ggttgtattaatatagttatatgt | Reverse | SEQ ID NO: 49 |
| BRCA1 Ext F | Tattttgagaggttgttgtttag | Forward | SEQ ID NO: 50 |
| BRCA1 Ext R | Aaacatcacttaaaccccctat | Reverse | SEQ ID NO: 51 |
| BRCA2 Ext F | Gttgggatgtttgataaggaat | Forward | SEQ ID NO: 52 |
| BRCA2 Ext R | Atcacaaatctatccectcac | Reverse | SEQ ID NO: 53 |
| P16 Ext F(3) | Aaagaggaggggttggttg | Forward | SEQ ID NO: 54 |
| P16 Ext R(5) | Aaccctctacccacctaaat | Reverse | SEQ ID NO: 55 |
| HIC1 Ext F | Tttagttgagggaaggggaa | Forward | SEQ ID NO: 56 |
| HIC1 Ext R | Aactacaacaacaactacctaa | Reverse | SEQ ID NO: 57 |

TABLE 2

Sequences of QM-MSP Primers (Used in Round 2 PCR of QM-MSP)

| Primer Name | QM-MSP Primer Sequences | | Orientation | Status |
|---|---|---|---|---|
| Cyclin D2 RT-FM | tttgatttaaggatgcgttagagtacg | SEQ ID NO: 13 | Forward | M |
| Cyclin D2 RT-RM | actttctccctaaaaaccgactacg | SEQ ID NO: 14 | Reverse | M |
| Cyclin D2 M Probe | aatccgccaacacgatcgaccta | SEQ ID NO: 15 | Reverse | M |
| Cyclin D2 RT-FUM | ttaaggatgtgttagagtatgtg | SEQ ID NO: 16 | Forward | U |
| Cyclin D2 RT-RUM | aaactttctccctaaaaaccaactacaat | SEQ ID NO: 17 | Reverse | U |
| Cyclin D2 UM Probe | aatccaccaacacaatcaaccctaac | SEQ ID NO: 18 | Reverse | U |
| RASSF1A RT-FM | gcgttgaagtegggggttc | SEQ ID NO: 19 | Forward | M |
| RASSF1A RT-RM | cccgtacttcgctaactttaaacg | SEQ ID NO: 20 | Reverse | M |

TABLE 2-continued

Sequences of QM-MSP Primers (Used in Round 2 PCR of QM-MSP)

| Primer Name | QM-MSP Primer Sequences | | Orientation | Status |
| --- | --- | --- | --- | --- |
| RASSF1A M Probe | acaaacgcgaaccgaacgaaacca | SEQ ID NO: 21 | Reverse | M |
| RASSF1A RT-FUM | ggtgttgaagttggggtttg | SEQ ID NO: 22 | Forward | U |
| RASSF1A RT-RUM | cccatacttcactaacttaaac | SEQ ID NO: 23 | Reverse | U |
| RASSF1A UM Probe | ctaacaaacacaaaccaaacaaaacca | SEQ ID NO: 24 | Reverse | U |
| TWIST RT-FM | gttagggttcggggcgttgtt | SEQ ID NO: 25 | Forward | M |
| TWIST RT-RM | ccgtcgccttcctccgacgaa | SEQ ID NO: 26 | Reverse | M |
| TWIST M-Probe | aaacgatttccttccccgccgaaa | SEQ ID NO: 27 | Reverse | M |
| TWIST RT-FUM (3) | ggtttggggtgttgtttgtatg | SEQ ID NO: 28 | Forward | U |
| TWIST-RT-RUM (3) | cccacctcctaaccaccctcc | SEQ ID NO: 29 | Reverse | U |
| TWIST UM Probe | aaacaatttccttccccaccaaaaca | SEQ ID NO: 30 | Reverse | U |
| RARB RT-FM | agaacgcgagcgattcgagtag | SEQ ID NO: 31 | Forward | M |
| RARB RT-RM | tacaaaaaaccttccgaatacgtt | SEQ ID NO: 32 | Reverse | M |
| RARB M Probe | atcctaccccgacgatacccaaac | SEQ ID NO: 33 | Reverse | M |
| RARB RT-FUM | ttgagaatgtgagtgatttgagtag | SEQ ID NO: 34 | Forward | U |
| RARB RT-RUM | ttacaaaaaaccttccaaatacattc | SEQ ID NO: 35 | Reverse | U |
| RARB UM Probe | aaatcctaccccaacaatacccaaac | SEQ ID NO: 36 | Reverse | U |
| HIN1 RT-FM | tagggaagggggtacgggttt | SEQ ID NO: 37 | Forward | M |
| HIN1 RT-RM | cgctcacgaccgtaccctaa | SEQ ID NO: 38 | Reverse | M |
| HIN1 M Probe | acttcctactacgaccgacgaacc | SEQ ID NO: 39 | Reverse | M |
| HIN1-RT-FUM (2) | aagtttttgaggtttgggtaggga | SEQ ID NO: 40 | Forward | U |
| HIN1 RT-RUM (2) | accaacctcacccacactccta | SEQ ID NO: 41 | Reverse | U |
| HIN1 UM Probe | caacttcctactacaaccaacaaacc | SEQ ID NO: 42 | Reverse | U |
| ACTB F | tggtgatggaggaggtttagtaagt | SEQ ID NO: 43 | Forward | Indep |
| ACTB R | aaccaataaaacctactcctcccttaa | SEQ ID NO: 44 | Reverse | Indep |
| ACTB Probe | accaccacccaacacacaataacaaacaca | SEQ ID NO: 45 | Reverse | Indep |
| ESR1 RT-FUM | tgttgtgtataattattttgagggt | SEQ ID NO: 58 | Forward | M |
| ESR1 RT-RUM | ccaatctaaccataaacctacaca | SEQ ID NO: 59 | Reverse | M |
| ESR1 UM Probe | caacaaccacaacattaaactcataaa | SEQ ID NO: 60 | Reverse | M |
| ESR1 RT-FM | cgtcgtgtataattatttcgagg | SEQ ID NO: 61 | Forward | U |
| ESR1 RT-RM | gatctaaccgtaaacctacgcg | SEQ ID NO: 62 | Reverse | U |
| ESR1 M Probe | cgacgaccgcgacgttaactcgt | SEQ ID NO: 63 | Reverse | U |
| APC1 RT-FUM | taaatacaaaccaaaacactccc | SEQ ID NO: 64 | Forward | M |
| APC1 RT-RUM | gttatatgttggttatgtgtgttt | SEQ ID NO: 65 | Reverse | M |
| APC1 UM probe | ttcccatcaaaaacccaccaattaac | SEQ ID NO: 66 | Reverse | M |
| APC1 RT-FM | aatacgaaccaaaacgctccc | SEQ ID NO: 67 | Forward | U |
| APC1 RT-RM | tatgtcggttacgtgcgtttatat | SEQ ID NO: 68 | Reverse | U |
| APC1 M Probe | cccgtcgaaaacccgccgatta | SEQ ID NO: 69 | Reverse | U |
| BRCA1 RT-FUM | tggtaatggaaaagtggggaa | SEQ ID NO: 70 | Forward | M |
| BRCA1 RT-RUM(4) | cccatccaaaaaatctcaacaaa | SEQ ID NO: 71 | Reverse | M |
| BRCA1 UM probe | ctcaccacacaatcacaattttaat | SEQ ID NO: 72 | Reverse | M |
| BRCA1 RT-FM | tttcgtggtaacggaaaagcg | SEQ ID NO: 73 | Forward | U |
| BRCA1 RT-RM | ccgtccaaaaaatctcaacgaa | SEQ ID NO: 74 | Reverse | U |
| BRCA1 M Probe | ctcacgccgcgcaatcgcaattt | SEQ ID NO: 75 | Reverse | U |
| BRCA2 RT-FUM | attttttgggtggtgtgtgtgtt | SEQ ID NO: 76 | Forward | M |
| BRCA2 RT-RUM | tcaaaaactcacaccacaaacc | SEQ ID NO: 77 | Reverse | M |
| BRCA2 UM Probe | aaccacataacaccataacacaacac | SEQ ID NO: 78 | Reverse | M |
| BRCA2 RT-FM | tttgattttcgggtggtgcgt | SEQ ID NO: 79 | Forward | U |
| BRCA2 RT-RM | tcaaaaactcgcgccacaaac | SEQ ID NO: 80 | Reverse | U |
| BRCA2 M Probe | aaccacgtaacgccgtaacgcga | SEQ ID NO: 81 | Reverse | U |

TABLE 2-continued

Sequences of QM-MSP Primers (Used in Round 2 PCR of QM-MSP)

| Primer Name | QM-MSP Primer Sequences | | Orientation | Status |
|---|---|---|---|---|
| P16 RT-FUM(2) | ttattagagggtggggtggattgt | SEQ ID NO: 82 | Forward | M |
| P16 RT-RUM | caaccccaaaccacaaccataa | SEQ ID NO: 83 | Reverse | M |
| P16 UM Probe | ctactccccaccacccactacct | SEQ ID NO: 84 | Reverse | M |
| P16 RT-FM(2) | ttattagagggtggggcggatcgc | SEQ ID NO: 85 | Forward | U |
| P16 RT-RM | gaccccgaaccgcgaccgtaa | SEQ ID NO: 86 | Reverse | U |
| P16 M Probe | agtagtatggagtcggcggcggg | SEQ ID NO: 87 | Reverse | U |
| HIC1 RT-FUM | gggttaggtggttagggtgtt | SEQ ID NO: 88 | Forward | M |
| HIC1 RT-RUM | taaccaaacacctccatcatatc | SEQ ID NO: 89 | Reverse | M |
| HIC1 UM Probe | aaacacacaccaaccaaataaaaaccat | SEQ ID NO: 90 | Reverse | M |
| HIC1 RT-FM | ggttaggcggttagggcgtc | SEQ ID NO: 91 | Forward | U |
| HIC1 RT-RM | ccgaacgcctccatcgtatc | SEQ ID NO: 92 | Reverse | U |
| HIC1 M Probe | cacacaccgaccgaataaaaaccgt | SEQ ID NO: 93 | Reverse | U |

The TaqMan™ probe used in the Example herein contains both a fluorescent reporter dye at the 5' end, such as 6-carboxyfluorescein (6-FAM: emission $\lambda_{max}$=518 nm) and a quencher dye at the 3' end, such as 6-carboxytetramethylrhodamine, (TAMRA; emission $\lambda_{max}$=582 nm). The quencher can quench the reporter fluorescence when the two dyes are close to each other, which happens in an intact probe. Other reporter dyes include but are not limited to VIC™ and TET™ and these can be used in conjunction with 6-FAM to co-amplify genes by quantitative real time PCR. For instance in round two QM-MSP, unmethylated (using a 6-FAM/TAMRA probe) and unmethylated RARβ (using a VIC/TAMRA probe) either can be co-amplified (FIG. 1) or can be assayed as single genes.

Thermal Cycling Parameters

The round two QM-MSP reactions are designed to be run as single gene reactions or in multiplex using automated equipment, as are other types of real time PCR. Thermal cycling parameters useful for performing real time PCR are well known in the art and are illustrated in the Examples herein. In certain embodiments, quantitative assays can be run using the same universal thermal cycling parameters for each assay. This eliminates any optimization of the thermal cycling parameters and means that multiple assays can be run on the same plate without sacrificing performance. This benefit allows combining two or more assays into a multiplex assay system, in which the option to run the assays under different thermal cycling parameters is not available.

Using the QM-MSP approach, it is possible to compile gene panels that are designed to address specific questions, or to provide intermediate markers or endpoints for clinical protocols. For example, when using de-methylating agents, a panel can be designed to query pathway-specific genes for their use as intermediate markers in specific trials of chemopreventive agents (Fackler M. J. et al. *J Mammary Gland Biol Neoplasia* (2003) 8:75-89).

In summary, the invention methods can be used to assess the methylation status of multiple genes, using only picograms of DNA. A cumulative score of hypermethylation among multiple genes better distinguishes normal or benign from malignant tissues. While the studies described herein show that some normal or benign tissue may have low-level gene promoter hypermethylation, it is also shown that distinct differences exist between the levels of normal and malignant tissues. Using QM-MSP, therefore, it is possible to objectively define the range of normal/abnormal DNA sequence hypermethylation in a manner that is translatable to a larger clinical setting. The invention methods may also be used to examine cumulative hypermethylation in benign conditions and as a predictor of conditions, such as various cancers and their metastases that are associated with DNA hypermethylation. The invention method may also predict conditions not associated with cancers, such as pre-eclampsia or eclampsia (Hueller H. M. et al. *M Clin Chem* (2004) 50:1065-1068).

In one embodiment, the primer extension reaction is a linear amplification reaction, wherein the primer extension reaction is performed over a number of cycles, and the linear amplification product that is generated is detected.

Due to the sensitivity of the invention methods, the first amplification product is optionally diluted from about 1:5 to about 1:$10^5$ and optionally separate aliquots of the first amplification product are further subjected to QM-MSP as described herein.

In real-time PCR, as used in the invention methods, one or more aliquots (usually dilute) of the first amplification product is amplified with at least a first primer of an internal amplification primer pair, which can selectively hybridize to one or more amplicon in the first amplification product, under conditions that, in the presence of a second primer of the internal amplification primer pair, and a fluorescent probe allows the generation of a second amplification product. Detection of fluorescence from the second amplification product(s) provides a means for real-time detection of the generation of a second amplification product and for calculation of the amount of gene specific second amplification product produced. Alternatively, the first amplification products used for the real time PCR reaction(s) may be contacted with both 1) a combination of a probe and DNA sequence-specific internal primer pair that recognizes only a methylated CpG island in the first amplicon and 2) a combination of a probe and DNA sequence-specific internal primer pair that recognizes an unmethylated CpG island for each of the DNA sequences in the panel of DNA sequences.

Thus, in one embodiment, the real-time PCR amplification in an invention two-step assay is, in fact, a group of real-time PCR reactions, which may be conducted together or using two separate aliquots of the first amplification product, for each of the first amplicons (i.e., for each DNA sequence in the panel that were selected for the assay). In this embodiment, determination of the methylation status of a DNA sequence, such as one containing a CpG island, employs both a methylation-determining and an unmethylation determining internal primer pair for each amplicon contained in the first amplification product, one to determine if the gene is unmethylated and one to determine if the gene is methylated. The real time PCR reactions in the second amplification step of the invention methods can conveniently be conducted sequentially or simultaneously in multiplex. Separate, usually dilute, aliquots of the first amplification reaction may be used for each of the two methylation status determining reactions. For example, the reactions can conveniently be performed in the wells of a 96 or 384 microtiter plate. For convenience, the methylated and unmethylated status determining second reactions for a target gene may be conducted in adjacent wells of a microtiter plate for high throughput screening. Alternatively, several genes, for example 2 to 5 genes, may be simultaneously amplified in a single real time PCR reaction if the probes used for each first amplicon are distinguishably labeled.

For example, two to five distinguishable fluorescence signals from the second amplification product(s) may be accumulated to determine the cumulative incidence or level of methylation of the DNA sequences, especially of CpG islands therein, in the several genes included in the assay. These cumulative results are compared with the cumulative results similarly obtained by conducting the two step QM-MSP assay on comparable DNA sequences (e.g., promoter DNA sequences) obtained from comparable normal tissue of the same type or types as used in the assay.

Any of the known methods for conducting cumulative or quantitative "real time PCR" may be used in the second amplification step so long as the first amplicons in the first amplification product are contacted with one or more members of a set of polynucleotide probes that are labeled with distinguishable optically detectable labels, one or more members of the set being designed to selectively hybridize to one or more of the DNA sequences being tested, while the set cumulatively binds to the various DNA segments being tested contained in the first amplicons of the first amplification product. In addition, the first amplicons may also be contacted with such a set of probes and one or more members of a set of DNA sequence-specific methylation status-dependent inner primer pairs, wherein the set of inner primer pairs collectively bind to the various first amplicons in the first amplification product. In round two QM-MSP, additional genes can be co-amplified provided that each gene primer set incorporates a different color fluorescent probe.

It should be recognized that an amplification "primer pair" as the term is used herein requires what are commonly referred to as a forward primer and a reverse primer, which are selected using methods that are well known and routine and as described herein such that an amplification product can be generated therefrom.

As used herein, the phrase "conditions that allow generation of an amplification product" or of "conditions that allow generation of a linear amplification product" means that a sample in which the amplification reaction is being performed contains the necessary components for the amplification reaction to occur. Examples of such conditions are provided in Example 1 and include, for example, appropriate buffer capacity and pH, salt concentration, metal ion concentration if necessary for the particular polymerase, appropriate temperatures that allow for selective hybridization of the primer or primer pair to the template nucleic acid molecule, as well as appropriate cycling of temperatures that permit polymerase activity and melting of a primer or primer extension or amplification product from the template or, where relevant, from forming a secondary structure such as a stem-loop structure. Such conditions and methods for selecting such conditions are routine and well known in the art (see, for example, Innis et al., "PCR Strategies" (Academic Press 1995);

Ausubel et al., "Short Protocols in Molecular Biology" 4th Edition (John Wiley and Sons, 1999); "A novel method for real time quantitative RT-PCR" Gibson U. E. et al. *Genome Res* (1996) 6:995-1001; "Real time quantitative PCR" Heid C. A. et al. *Genome Res* (1996) 6:986-994).

As used herein, the term "selective hybridization" or "selectively hybridize" refers to hybridization under moderately stringent or highly stringent conditions such that a nucleotide sequence associates with a selected nucleotide sequence but not with unrelated nucleotide sequences. Generally, an oligonucleotide useful as a probe or primer that selectively hybridizes to a selected nucleotide sequence is at least about 15 nucleotides in length, usually at least about 18 nucleotides, and particularly about 21 nucleotides in length or more in length. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual" (Cold Spring Harbor Laboratory Press 1989)).

The phrase "comparable normal tissue" as used herein means that histologically apparently normal tissue(s) are collected from tissue site(s) in the subject adjacent to the site(s) from which the tumor tissue is collected. Alternatively, the "comparable normal tissue" can be collected from sites(s) of unrelated healthy donors that anatomically related to the site(s) of subject tumor tissue used (e.g., same tissue type), or the results representing the accumulated incidence of the tumor marker in anatomically related apparently normal tissue site(s) of normal subjects can be compared with the results of the assay obtained from the subject's own tumor-associated tissue. Similarly, the phrase "a comparable normal DNA sample" as used herein means that the plurality of genomic DNA sequences that is being tested for methylation status, such as in a plant or insect, is matched with a panel of genomic DNA sequences of the same genes from a "normal" organism of the same species, family, and the like, for comparison purposes. For example, a substantial cumulative increase or decrease in the methylation level in the test sample as compared with the normal sample (e.g., the cumulative incidence of the tumor marker in a test DNA panel compared with that cumulatively found in comparable apparently normal tissue) is a reliable indicator of the presence of the condition being assayed.

The invention methods can be used to assay the DNA of any mammalian subject, including humans, pets (e.g., dogs, cats, ferrets) and farm animals (meat and dairy), and race horses. The invention methods can also be used to assay the DNA of plants ("DNA methylation in plants" Finnegan E. J. et al. *Annu Rev Plant Physiol Plant Mol Biol* (1998) 49:223-247) and insects ("DNA methylation learns to fly" Frank Lyko *Trends in Gen* (2001) 17:169-172).

The invention methods are illustrated using primary breast cancer as an example (Fackler M. J. et al, *Int. J. Cancer* (2003) 107:970-975; Fackler M. J. et al. *Cancer Res* (2004) 64:4442-4452). In breast cancer, samples can be collected from such tissue sources as ductal lavage and nipple aspirate fluid where the DNA amount is limiting, for example as little as about 50 to about 100 cells, as well as in larger samples, such as formalin-fixed paraffin-embedded sections of core biopsies. The maximum input DNA is approximately 600 ng. Using invention methods of QM-MSP, the level and incidence of hypermethylation CpG islands in RASSF1A, TWIST, Cyclin D2, HIN1, and RAR-β, genes in samples where DNA is limiting or when extreme sensitivity is desired can be co-amplified for the purpose of detecting progression of primary breast cancer in a subject. Scoring the cumulative methylation of these gene promoters within a sample gives high sensitivity and specificity of detection of primary breast cancer and a global indication of promoter hypermethylation in tumors relative to normal tissue. The invention methods are designed to evaluate samples that contain extremely limited amounts of DNA, such as those from ductal lavage or nipple aspiration. In the process, the extent of gene hypermethylation in primary breast cancer has been evaluated and the method is readily adaptable to clinical testing. Although this technique is illustrated with respect to breast tissues, the technique can be used to evaluate gene (e.g., gene promoter) hypermethylation within a wide range of tissues.

Recently it has been shown that some of the genes whose promoters are most frequently hypermethylated (30-90%) in breast carcinomas, but not in normal breast epithelium or circulating blood cells, are Cyclin D2, RARB, TWIST, RASSF1A and HIN1. Widschwendter and Jones (supra) reviewed over 40 genes lost in breast cancer due to promoter hypermethylation. A study of 103 cases of breast cancer recently observed that in 100% of cases of invasive carcinoma, and in 95% of cases of ductal carcinoma in situ (DCIS) one or more gene promoters in a panel of markers consisting of RASSF1A, HIN1, RAR-β, Cyclin D2 and TWIST were hypermethylated. In fact, the vast majority of tumors (80%) have promoters that are hypermethylated for two or more of these five genes, prompting the observation that tumor tissue may have a pattern of methylation of multiple promoters (Fackler M. J. et al. *Int J Cancer* (2003) in press, online). Thus, it was conceived that profiling the cumulative methylation of multiple gene promoters associated with a particular type of cancer, such as primary breast cancer, would serve to better distinguish benign from malignant tissues and to provide a more powerful approach than characterizing the status of one or more gene markers (Fackler M. J. et al. *Cancer Res* (2004) 64:4442-4452).

Studies also have demonstrated the feasibility of assessing gene promoter hypermethylation in ductal lavage (DL) samples (Evron E. et al. *Lancet* (2001) 357:1335-1336). These studies found TWIST, Cyclin D2 or RARB gene promoter hypermethylation in cells derived from subjects with ductal carcinoma. However, the status of more than 3 genes in any single sample could not be assessed because of the limited available DNA. For example, the DL samples used in the current study contained 50-1000 epithelial cells such that assessment of the status of many genes would be virtually impossible. Therefore, a new strategy was designed to better evaluate sources of material where DNA is limited (e.g. ductal lavage, plasma, fine-needle or core biopsy, or nipple aspiration fluid).

Figure 9:
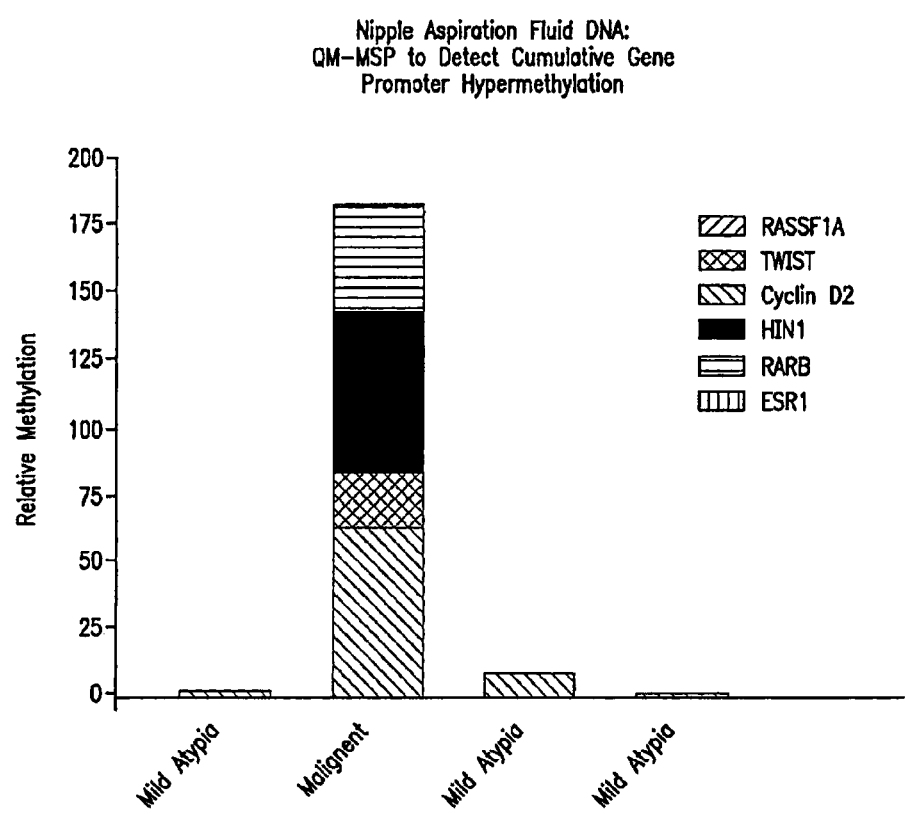
FIG. 9 is a bar graph showing cumulative promoter hypermethylation in ductal cells obtained within nipple aspiration fluid for RARβ, RASSF1A, TWIST, Cyclin D2, HIN1, and ESR1 genes. The cumulative methylation of the 50-1000 cells is indicated. Cells showed either mild atypia (n=3) or appeared malignant (n=1) by cytology. The relative level of methylation of each gene is indicated by the height of the bar. Total possible units=600 (6 genes×100%).
Figure 10:
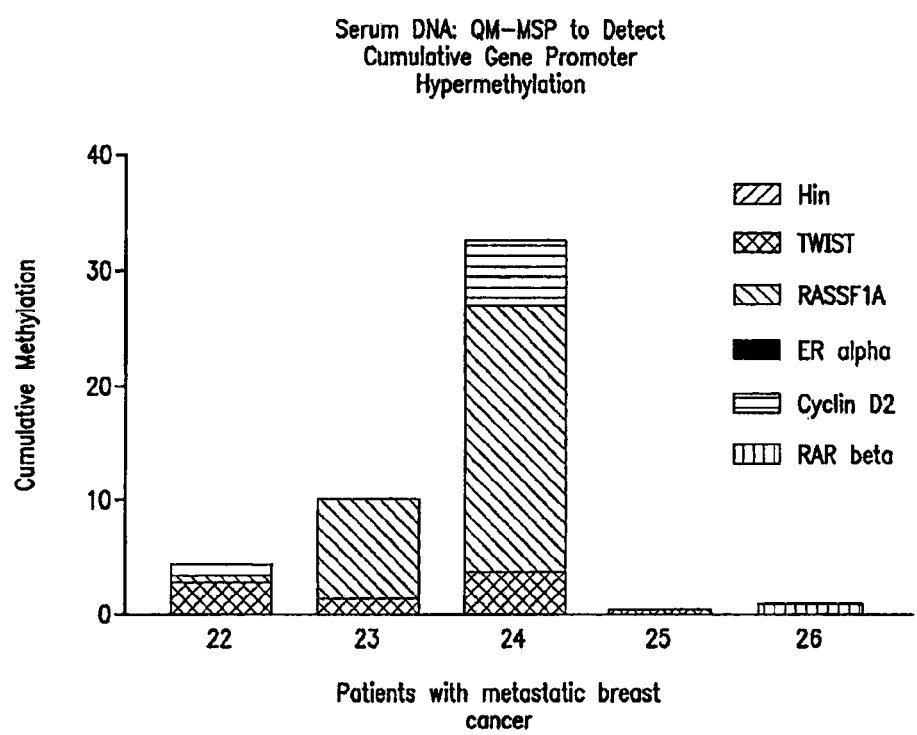
FIG. 10 is a bar graph showing cumulative promoter hypermethylation in serum derived from patients (n=5) with metastatic breast cancer. Shown is the cumulative methylation of RARβ, RASSF1A, TWIST, Cyclin D2, HIN1, and ESR1 genes. The relative level of methylation of each gene is indicated by the height of the bar. Total possible units=600 (6 genes×100%).

While QM-MSP was performed in a 96 well platform in the Examples illustrating the invention, a 384 well platform, or larger can be used for high throughput if QM-MSP is formatted for a larger setting. The QM-MSP technique is applicable to frozen or archival paraffin-embedded clinical tissues (FIGS. 5-7), as well as ductal lavage material (FIGS. 8, 11-12), plasma (data not shown), serum (FIGS. 10-11), nipple aspiration fluid (FIG. 9), and fine needle aspirates (FIGS. 11 and 13). Other sources of sample DNA are also suitable for QM-MSP monitoring including but not limited to core tissue biopsies, bronchial washings, buccal cavity washings, cervical scrapings, prostatic fluids, and urine. Conditions that are unrelated to cancer which are suitable for monitoring by the invention include but are not limited to eclampsia and pre-eclampsia ("DNA Methylation Changes in Sera of Women in Early Pregnancy Are Similar to Those in Advanced Breast Cancer Subjects" Muller H. M. et al. *Expert Rev Mol Diagn* (2004) 3:443-458.

In a study of 14-28 tissue samples per group, the extent of gene promoter hypermethylation between normal tissues (derived from reduction mammoplasty) and malignant tissues (primary invasive ductal carcinoma) for RASSF1A, TWIST, Cyclin D2, and HIN1 (FIG. 5 and Table 5) was studied (Fackler M. J. et al. *Cancer Res* (2004) 64:4442-4452). Significant differences were observed in the level of promoter hypermethylation between normal and tumor tissues for each of these four genes, based on comparison of mean and median normal values (Table 5).

Importantly, one of the powers of the invention method of QM-MSP is that it provides a means for defining the normal range of promoter methylation, as shown for RASSF1A, TWIST, HIN1 and Cyclin D2 genes in normal breast tissue (Table 5 and FIG. 5) (Fackler M. J. et al. *Cancer Res* (2004) 64:4442-4452). Techniques that give higher sensitivity usually also give higher "background," picking up signals that are missed by other methods. This was also observed in our current study, where a higher incidence of methylation in normal mammoplasty was observed than previously (Fackler M. J. et al. *Int J Cancer* (2003) in press, online) found using the gel-based MSP. Even so, with QM-MSP, the median of promoter methylation was 0% M for all genes. By setting an upper threshold for normal, the occasional low-level methylation that occurs in some normal tissues is acknowledged and criteria are set that define "positive" results as being in tumor. In the current study, cutoffs were established such that approximately 5-10% of normal samples fell above the cutoff. Using this criterion, the incidence of positive showing in tumor tissue was 68% for RASSF1A, 67% for TWIST, 57% for Cyclin D2, and 57% for HIN1 (Table 5).

More informative than evaluating the methylation status of a single gene, studies of cumulative multi-gene promoter hypermethylation indicated that striking differences exist between normal and malignant tissues (FIGS. 6A and 6B)) (Fackler M. J. et al. *Cancer Res* (2004) 64:4442-4452). The panel of four genes (RASSF1A, TWIST, Cyclin D2, and HIN1) was amplified in 9 normal breast tissues and 19 primary carcinomas and the cumulative amount of gene promoter hypermethylation was determined for each of these samples (FIGS. 6A and 6B and Table 6). There was a highly significant (p=0.0002) difference between levels of cumulative gene promoter hypermethylation in normal tissues and that in malignant tissues when evaluating RASSF1A, TWIST, Cyclin D2 and HIN1 together as a panel. The invention methods employing cumulative methylation profiling of a panel of four genes was able to detect 84% of tumors; whereas single gene analyses yielded positive results in only 57-68% cases, depending on the gene analyzed (FIGS. 5 and 6A-B). To our knowledge, this result is the first study to describe quantitation of cumulative methylation of gene promoters associated with a particular type of carcinoma, and shows its importance in distinguishing between normal and tumor tissues (Fackler M. J. et al. *Cancer Res* (2004) 64:4442-4452).

Molecular alterations in histologically normal appearing breast tissue adjacent to tumor have been previously reported, although their significance is not yet clear (Umbricht C. B. et al. *Oncogene* (2001) 20:3348-3353; Deng G. et al. *Science* (1996) 274:2057-2059; Heid C. A. et al. *Genome Res* (1996) 6:986-94). In the present study, the cumulative amount of gene promoter hypermethylation for RASSF1A, TWIST, Cyclin D2, and HIN1 gene promoters was studied in 6 pairings of tumor and apparently histologically normal adjacent tissue (Table 6, FIG. 7). All 6 genes showed hypermethylation in tumor tissue. The adjacent normal tissues were also positive for promoter hypermethylation in 4 of 6 individuals, although the levels were considerably lower than in the nearby tumor tissue (p=0.01, based on the Mann-Whitney test). Therefore, this study suggests that adjacent normal tissue contains hypermethylated genes, albeit at a lower level than the adjacent tumor tissues. Thus, elevated methylation in histologically normal tissue adjacent to tumor may be an indicator the state of tissue cell populations undergoing disease. The high degree of sensitivity, precision and linearity that may be achieved using the invention methods, makes it possible to quantify disease progression, for example, the pre-existence of molecular alterations that render the tissue at a higher risk for breast cancer, or are normal age-related changes. It is important to note that no age-related abnormalities in these genes were observed in studies conducted as described herein (our unpublished data).

Application of the invention QM-MSP methods to ductal washings showed that it is possible to co-amplify up to 5 genes (FIG. 8 and Table 7), from limited amounts of DNA (Fackler M. J. et al. *Cancer Res* (2004) 64:4442-4452). Using this approach, it was observed that most genes were successfully amplified in the samples. Analysis for cumulative gene promoter hypermethylation showed that little or no methylation was detected in the majority of samples taken from individuals having benign lesions (1 of 8 cases had low level methylation). By comparison, 2 of 4 samples with features of ductal carcinoma in situ (DCIS) had extremely high levels of cumulative gene hypermethylation. It can be concluded from this analysis that QM-MSP can be applied to analysis of multi-gene promoter hypermethylation in cells derived from washings of breast ducts. Furthermore, the QM-MSP method can be applied to investigate multiple gene promoter hypermethylation that could not have been evaluated using conventional MSP methods due to limiting quantities of input DNA being available.

Of interest, however, 2 of 4 cases of DCIS failed to demonstrate any detectable methylation when tested according to the invention methods (FIG. 8, Table 7)) (Fackler M. J. et al. *Cancer Res* (2004) 64:4442-4452). In our previous study of 44 histological sections of DCIS tissue, 95% of the samples were hypermethylated for one or more of the RASSF1A, TWIST, Cyclin D2, HIN1, and RARB gene promoters (Fackler M. J. et al. *Int J Cancer* (2003) in press, online). The reasons for the failure to detect methylation in all four samples could be that the number of cells present in ductal washings was below our sensitivity of detection. Conversely, although from the same breast, the washings could have been from a duct that was not the one bearing the DCIS. Additional promoters associated with breast cancer tissue, APC1, ESR1, BRCA1, BRCA2, P16 and HIC1 already have been added to this multiplex reaction panel successfully and are undergoing detailed examination (FIGS. 9-13; Primer SEQ ID 46-93) FIGS. 1-2).

The invention is further described by the following example, which is meant to illustrate, and not to limit, the invention.

Example 1

Materials and Methods

Probes as shown in Tables 1 and 2 above were purchased from Applied Biosystems (Applied Biosystems, Foster City, Calif.) and other primers were purchased from Invitrogen (Invitrogen Corporation, Carlsbad, Calif.). Q-MSP primers and probes for β-Actin and methylated Cyclin D2 and RASSF1A genes were described in Lehmann et al. (supra). All other sequences were designed in known regions of promoter hypermethylation in breast carcinoma.

Tissues and Cells:

Paired primary tumors and adjacent normal tissues (frozen tissue), paraffin-embedded normal breast tissue obtained from routine reduction mammoplasty, and primary breast cancer tissues were obtained from the Surgical Pathology archives of The Johns Hopkins Hospital after receiving approval from the institutional review board. The percentage of epithelial cells ranged from 20-50%. Ductal lavage (DL) samples were obtained from the Johns Hopkins Cytopathology Laboratory. Human sperm was obtained from a normal donor. The MDA-MB231 breast cancer cell line was obtained from ATCC and cultured as directed.

Sectioning and DNA Extraction from Formalin-Fixed Paraffin-Embedded Tissue.

The composition of the unstained slides from each archival formalin-fixed, paraffin-embedded tissue block was confirmed by histopathological examination of surrounding hematoxylin and eosin (H & E) section. For each tumor, the lesion was identified on an initial H & E section, and confirmed to remain on a serial H & E section taken following preparation of unstained sections for nucleic acid extraction. For DNA extraction, one 5-micron tissue section was deparaffinized in xylene (20 min), scraped from the slide and extracted in 100 µl TNES (10 mM Tris, pH 8.0, 150 mM, NaCl, 2 mM EDTA, 0.5% SDS) containing 40 µg proteinase K for 16 hr at 50° C. The tissue extract was heat inactivated at 70° C. for 10 min and clarified by centrifugation at 14K rpm for 10 min; 50 µl of the supernatant was used directly as a source of DNA for sodium bisulfite treatment.

For extraction of DNA from 50-1000 ductal cells, ductal washings were collected in up to 20 ml of isotonic saline. The cellular suspension was cytocentrifuged onto glass slides and stained with Papanicolaou's stain (Pap Stain) for diagnostic cytological evaluation. The slide coverslip was then removed by treatment with xylene, and cells were scraped and transferred to 50 µl TNES containing 40 µg/ml proteinase K, and 200 ng of salmon sperm carrier DNA.

For frozen tissues and MDA-MB231 cells to be used as methylated control DNA, DNA was extracted with phenol/chloroform using a procedure described in Maniatis T. et al. "Molecular cloning: a laboratory manual" (New York Cold Spring Harbor 1982).

Human sperm DNA (HSD) (unmethylated control) was purified using the PUREGENE® DNA Purification Kit (Gentra Systems, Minneapolis Minn.) with minor modifications to the manufacturer's protocol. Briefly, fresh seminal fluid was diluted to 25 ml with TE, and incubated at 37° C. for 1 hr. The specimen was centrifuged at 3000 rpm for 15 min at 4° C. The cellular pellet was rigorously vortexed, resuspended in Cell Lysis Solution containing dithiothreitol and proteinase K, and incubated at 55° C. overnight. The cell lysate was incubated with RNase A solution for 1 hr at 37° C. Proteins were salted out. The DNA was precipitated with isopropanol, washed in ethanol, and rehydrated with DNA Hydrating Solution (supplied by the manufacturer). HSD was stored at 4° C.

Sodium Bisulfite Treatment of DNA

Tissue, control and cell line DNAs were treated with sodium bisulfite and analyzed using methylation-specific PCR (MSP) as described by Herman et al. (supra). This process converts non-methylated cytosine residues to uracil, while methylated cytosines remain unchanged. Bisulfite-modified samples were aliquoted and stored at −80° C.

Probes and Primers
Quantitative Multiplex Methylation-Specific Polymerase Chain Reaction (MSP)

The QM-MSP procedure required two sequential PCR reactions (FIG. 1). In the first PCR reaction (the multiplex step) (RXN 1) 1 μl sodium bisulfite-treated DNA was added to 24 μl reaction buffer [1.25 mM dNTP, 16.6 mM $(NH_4)_2SO_4$, 67 mM Tris, pH 8.8, 6.7 mM MgCl2, 10 mM β-mercaptoethanol, 0.1% DMSO, and 2.5-5 U Platinum Taq (Invitrogen)] containing 100 ng of each gene specific primer pair (forward and reverse primer for each of the six gene promoters RASSF1A, RAR-β, TWIST, Cyclin D2, HIN1, and β-Actin control) (SEQ ID NOS:1-12). The PCR conditions were 95° C. for 5 min, followed by 35 cycles of 95° C. for 30 sec, 56° C. for 30 sec, and 72° C. for 45 sec, with a final extension cycle of 72° C. for 5 min. The PCR products were diluted up to 125 μl with water and stored at −20° C. For this QM-MSP reaction, the total input DNA concentration ranged from 50 ng purified DNA) to ~40 pg (for some ductal lavage samples).

For the second reaction (round two of the QM-MSP step) (Rxn 2), 1 μl of the diluted PCR product from reaction 1 was used directly, or after further dilution of up to 1:$10^4$ (when 50 ng DNA was used in reaction 1). The diluted DNA was added to the real-time-MSP reaction buffer containing 16.6 mM $(NH_4)_2SO_4$, 67.0 mM Tris, pH 8.8, 6.7 mM $MgCl_2$, 10.0 mM (β-mercaptoethanol, 0.1% DMSO, 200 μM dNTP, 1.25 U Platinum DNA Taq Polymerase (Invitrogen) and IX ROX (Invitrogen). 600 nM of each of two internal primers (forward and reverse) (SEQ ID NOS: 13, 14, 16, 17, 19, 20, 22, 23, 25, 26, 28, 29, 31, 32, 34, 35, 37, 38, 40, 41, 43 and 44) and 200 nM labeled probes (Applied Biosystems) (SEQ ID NOS:15, 18, 21, 24, 27, 30, 33, 36, 39, 42 and 45) were also present. The separate reactions were carried out in wells of a 96-well reaction plate in an ABI Prism 7900HT Sequence Detector (Applied Biosystems). The reactions proceeded at 95° C. for 5 min, then 35 cycles of 95° C. for 15 s and 60-65° C. (depending on the primer set) for 1 min, with a 10 min extension at 72° C. For each gene included in the reaction plate, the following were used to create standard curves and to provide controls: 1) serially diluted stock multiplexed HSD/231DNA (described below, to establish a standard curve), 2) 40,000 copy (40 K) controls, 3) no template control and 4) a known DNA (mixed to 1% methylated copies; Table 3) to ensure consistency between runs. In addition, 5) 100% methylated (MDA-MB231 cell DNA), 6) 0% methylated (HSD DNA, 99-100% unmethylated), and 7) sample lacking template DNA from the first PCR reaction (diluted 1 to 5) were present. All of the above samples were analyzed with primer sets for both methylated and unmethylated DNA.

Preparation of Standards.

A stock of multiplexed DNA was prepared as follows: PCR was performed in a reaction mix that contained all six gene primer pairs as well as a mixture of 50 ng each of sodium bisulfite treated genomic MDA-MB231 and HSD DNA. Serial dilutions of this stock DNA were used to establish a standard curve in the quantitative real-time PCR reaction (Rxn 2). To do this, the cycle threshold ($C_T$; the cycle in which the signal exceeds the background) of each dilution was determined during the round two QM-MSP reaction and then plotted to generate a line for the standard curve. For each reaction plate, the standards were diluted from the same stock stored frozen at −80° C. for all assays and new dilutions were made each time.

Copy Number Controls.

For the preparation of this control, unmethylated (U) or methylated (M) genomic DNAs were amplified for each gene in a separate reaction using a gene-specific pair of methylation-status specific external primers (Forward, Reverse and Probe) and 50 ng of sodium bisulfite-treated genomic DNA derived from either MDA-MB231 (100% methylated) or human sperm DNA (100% unmethylated). A single band was observed by gel electrophoresis. The reaction products were then purified with a Qiaquick® PCR purification kit (Qiagen Inc., Valencia, Calif.), and eluted in 100 μl water. The eluate was quantitated using the NanoDrop spectrophotometer (NanoDrop Technologies, Montchanin, Del.) and the DNA concentration (μg/μl) was determined based on the $OD_{260}$. The molecular weight (μg/μmol) of the PCR product was calculated using Biopolymer Calculator v4.1.1 (C. R. Palmer available on the world wide web at the address paris.chem.yale.edu/extinct). Using Avogadro's definition (1 μmol=$6\times10^{17}$ molecules), DNA copies per microliter were calculated: DNA copies/μl=(DNA concentration) ($6\times10^{17}$ molecules)/molecular weight. The concentration of each gene template control was adjusted to $3\times10^{10}$ copies per microliter in 1 mg/ml salmon sperm carrier DNA, and stored at −80° C. Unmethylated and methylated DNA for each of the six genes were obtained and stored separately. A cocktail was then prepared that contained $4\times10^6$ copies per microliter of each gene in 1 mg/ml salmon sperm DNA. For each reaction plate, the DNA cocktail was then diluted 100-fold to 40,000 copies per well. Salmon sperm DNA did not interfere with the PCR reaction (data not shown). A known quantity of DNA (40,000 copies per well, denoted "40K" control), prepared as described above, was used to transform the standard curve to represent copy number. The cycle threshold ($C_T$) of the 40 K control was determined during the Q-MSP reaction and plotted on the line obtained for the standard curve. The copy number for each dilution was then "back calculated," based on where the 40K $C_T$ intersected the standard curve. Sample 40 K had approximately equal amounts of unmethylated and methylated DNA for each of the six genes along with carrier salmon sperm DNA (10 μg/ml).

Calculation of % Methylation

The relative amount of methylation for each unknown sample was calculated as

% M=(100)(# copies M/# copies methylated+unmethylated DNA). To determine the # copies of methylated and unmethylated DNA, sample DNA was mixed with Q-MSP reaction buffer following the multiplex reaction, then assayed with methylated primers and unmethylated primers (in separate wells) in the round two QM-MSP reaction, and a $C_T$ was determined for each. Using the ABI Prism SDS 2.0 software supplied by Applied Biosystems with the 7900 HT Sequence Detector, the number of copies of methylated and unmethylated DNA was extrapolated from the respective standard curves using the sample $C_T$ and applying the absolute quantification method according to the manufacturer's directions. Only values falling within the range covered by the standard curve were accepted.

Statistical Analysis and Graphical Representation of Data.

Statistical analyses and plotting of data were performed using GraphPad Prism (GraphPad Software Inc., San Diego, Calif.). P values<0.05 were considered significant and all tests were two-tailed. The nonparametric Mann-Whitney test was used to test whether the samples are from identical distributions, indicating their medians are equal. Sample means were compared using the unpaired t test, assuming unequal variances (Welch's correction). For testing of means, data were transformed as a function of $Ln_e$ (% M+1) where stated to fulfill the assumption of normality. The Fisher's exact test was used to test whether the differences between the incidence of positivity for methylation in tumor and normal were significant.

Results

Quantitative-Multiplex PCR (QM-MSP) Assay is a Two-Step Reaction:

Validation of the QM-MSP Assay—

Multiplex PCR, the first step in the QM-MSP assay, was accomplished by performing two sequential PCR reactions as shown schematically in FIG. 1). In the first PCR reaction, a cocktail of six pairs of gene-specific primers were used to co-amplify Cyclin D2, RARB, TWIST, RASSF1A, HIN1, and Actin (as a control) (Tables 1 and 2). These external primer pairs were complimentary to the sequences flanking the CpG islands that were to be queried in the second PCR reaction. External primers were selected to exclude CG dinucleotides, thereby rendering DNA amplification independent of the methylation status.

Both U and M Primers are Equally Efficient in Amplifying DNA—

Figure 2A:
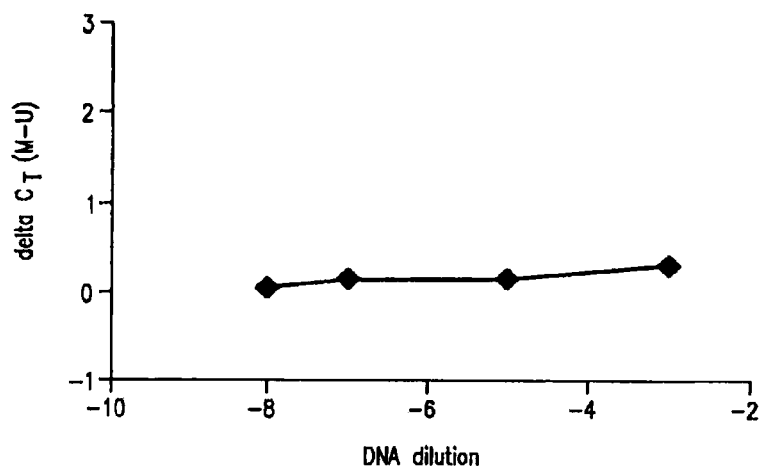
FIGS. 2A-B are graphs showing validation of QM-MSP using RASSF1A unmethylated (U) and methylated (M) primer sets to amplify serially diluted fragments of multiplexed standard stock HSD/231 DNA. The cycle threshold ($C_T$) was determined for each dilution of DNA.
Figure 2B:
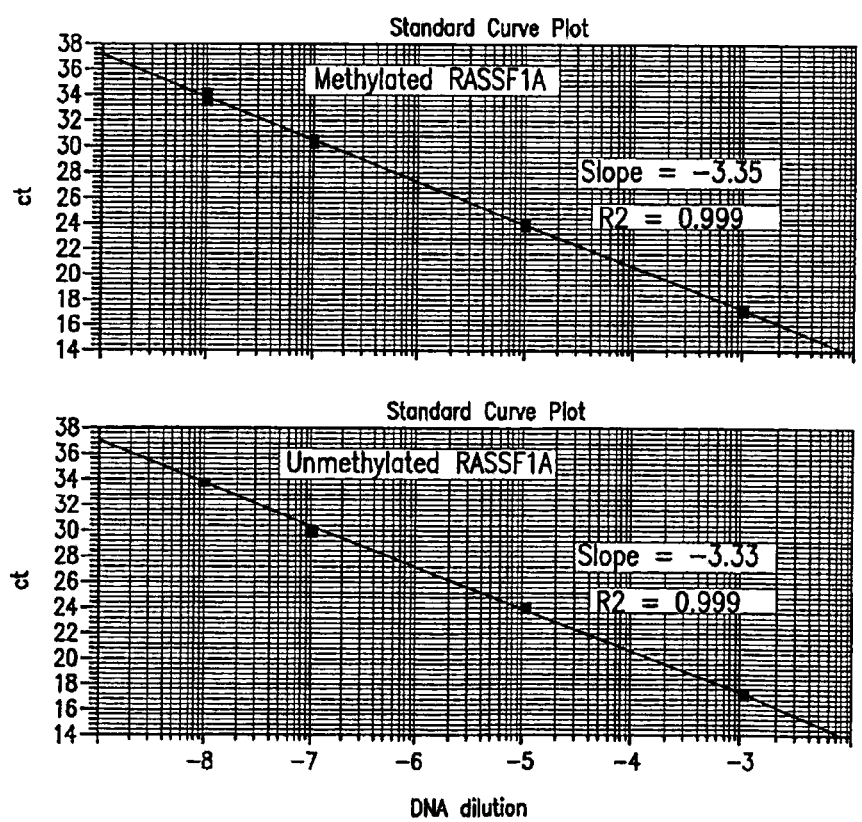

Primer sets specifically for methylated (M) and unmethylated (U) DNA were designed for comparable performance; to confirm this, the delta $C_T$ ($C_T$ M–$C_T$ U) was plotted as a function of sample dilution over a wide range of dilutions (10 to $10^{-8}$) of the standard stock HSD/231 DNA. Analyses were performed as is shown for RASSF1A in FIGS. 2A-B. The delta $C_T$ was approximately the same for all dilutions, as shown by the horizontal nature of the line, indicating that the primer sets were equally efficient over 5 logs of template quantities (FIG. 2A). In addition, for both unmethylated and methylated standard curves the slopes are approximately –3.33, which is reflective of a two-fold increase in PCR product per cycle during the linear phase of real-time PCR. Finally, a correlation coefficient (R2) of 0.999 indicates that linearity exists over the entire range of template concentration as shown in FIG. 2B). Similar results were obtained for the other five genes in our study (data not shown).

Specificity and Sensitivity—

To assess the sensitivity and specificity of the QM-MSP method, a mixing experiment was performed using column-purified, PCR-amplified fragments of sodium bisulfite-modified DNA as template as shown in Table 3 below. The amount of unmethylated DNA was kept constant (100,000 copies per well) and the amount of methylated DNA was decreased (1000-0.1 copy per well). Although the general efficiency of real time PCR is known to fall off at less than 100 copies, it was expected that some level of methylation would be detected below 100 copies, although probably not in a linear manner. For RASSF1A and TWIST, methylation was detected at 1 methylated in 100,000 unmethylated copies and for Cyclin D2 and HIN1 at 10 methylated in 100,000 unmethylated copies. Therefore, the overall sensitivity of the method is 1-10 in 100,000.

TABLE 3

Determination of the sensitivity of QM-MSP.

| | % Methylation[c] | | | |
|---|---|---|---|---|
| | RASSF1A | Twist | Hin-1 | Cyclin D2 |
| # Copies M and U Template[a] | | | | |
| 1000/100,000 | 0.9220 | 2.7604 | 4.8024 | 1.5760 |
| 100/100,000 | 0.0602 | 0.2482 | 0.6273 | 0.1525 |
| 10/100,000 | 0.0078 | 0.0272 | 0.0024 | 0.0025 |
| 1/100,000 | 0.0072 | 0.0012 | 0.0000 | 0.0000 |
| .1/100,000 | 0.0000 | 0.0000 | 0.0000 | 0.0000 |
| HSD (100% U control) | 0.0000 | 0.0003 | 0.0000 | 0.0000 |
| 231 (100% M control) | 99.9981 | 100.0000 | 100.0000 | 100.0000 |
| Water | 0.0000 | 0.0000 | 0.0000 | 0.0000 |
| # Copies M and U[b] | | | | |
| 300/29700 | 0.7823 | 1.2190 | | |
| 30/2970 | 0.7195 | 0.9376 | | |
| 3/297 | 0.2390 | 0.1451 | | |

[a,b]Purified methylated (M) and unmethylated (U) stock DNA template were mixed in the proportions indicated.
[a]Unmethylated DNA was kept constant as the amount of methylated DNA was decreased.
[b]A 1% M control was kept constant as the total quantity of DNA decreased.
[c]The % Methylation of RASSF1A, TWIST, HIN1 and Cyclin D2 from the QM-MSP assay is shown. The assay senstivity is 1-10 in 100,000 for methylated DNA and detects as few as 1-3 copies of methylated DNA.

The highly specific performance of the methylated primers was demonstrated using the HSD control (100% unmethylated DNA), and 0.1/100,000 sample (diluted to <1 copy of methylated in the presence of 100,000 copies of unmethylated DNA), both of which showed 0% M in the QM-MSP reaction (Table 3, FIG. 3). Likewise, no unmethylated signal (0% U) was detected in MDA-MB231 methylated DNA control (100% methylated DNA). It was expected that the 1000/100,000 sample would be read as 1% methylated (1000 copies of methylated and 100,000 copies of unmethylated). That some samples were slightly higher (e.g. 4.8% for HIN1, 2.8% for TWIST) probably reflects difficulty in accurately diluting samples from a starting concentration of $3 \times 10^{10}$ copies per μl (diluted over 5-10 logs).

To characterize the behavior of the QM-MSP assay below the lower limit of linearity (specifically, whether a 1% M template produces a 1% M assay result as the total quantity of DNA template diminishes), a "1%" standard was serially diluted and samples were tested beginning at a template quantity estimated to contain 300 copies of methylated DNA to ~29700 unmethylated copies (300/29700), using column-purified DNA as a template (Table 3). The lowest quantity tested contained three copies methylated to ~297 copies unmethylated DNA (3/297). The results for RASSF1A and TWIST (Table 3) revealed that at ratios of 300/29700 and 30/2970 total copies, the assay result (% M) was approximately 1% for each. Methylation was still detectable at the lowest ratio template quantity tested, at three copies of methylated DNA, consistent with the previous experiment (1 copy of methylated DNA was detected in 100,000 copies of unmethylated DNA). We found a bias towards underreporting of the % M below 30 copies of methylated DNA, probably reflecting the relative lack of efficiency of the methylated reaction compared to the unmethylated reaction that contained nearly 100-fold more copies of the gene (Table 3). This result was predicted, since linearity is generally known to be lost below 100 copies of DNA template in real-time PCR.

Genomic DNA is a more challenging template than PCR-amplified DNA because breakage of genomic DNA is known to occur in the process of sodium bisulfite conversion. To evaluate the sensitivity of the QM-MSP method with genomic DNA, DNA mixing experiments were performed with approximately 40 pg methylated DNA (~13 copies derived from 231 cell DNA) and 600-60000 pg unmethylated genomic DNA (~200-20,000 copies of HSD). Using the QM-MSP method, 40 pg of methylated RASSF1A genomic DNA was easily detected even in the presence of a 1500-fold excess of unmethylated DNA as shown in FIG. 4), when the conversion estimate of 6 pg/2 copies/cell of DNA was used.

Comparison Between QM-MSP and Q-MSP

It is possible that performing a two-step multiplex PCR method could yield results that differed from those obtained with a direct one-step PCR method because of the addition of the multiplex step. We performed QM-MSP and direct Q-MSP assay on a panel of five tumor DNAs and calculated the percentage of methylation by the (U+M) method to estimate total DNA. With few exceptions, there was excellent concordance between the percentage of methylation values obtained for the RASSF1A, TWIST, HIN1 or Cyclin D2 genes (Table 4).

TABLE 4

Comparison between Q-MSP and QM-MSP

| | % M | |
|---|---|---|
| | Q-MSP | QM-MSP |
| RASSF1A | | |
| 1 | 95 | 99 |
| 2 | 80 | 81 |
| 3 | 39 | 41 |
| 4 | 12 | 21 |
| 5 | 28 | 34 |
| HSD | 0 | 0 |
| 231 | 100 | 100 |
| Water | 0 | 0 |
| TWIST | | |
| 1 | 96 | 70 |
| 2 | 0 | 0 |
| 3 | 54 | 26 |
| 4 | 1 | 3 |
| 5 | 0 | 5 |
| HSD | 0 | 0 |
| 231 | 100 | 100 |
| Water | 0 | 0 |
| HIN1 | | |
| 1 | 95 | 82 |
| 2 | 81 | 74 |
| 3 | 82 | 48 |
| 4 | 41 | 16 |
| 5 | 47 | 43 |
| HSD | 0 | 0 |
| 231 | 100 | 100 |
| Water | 0 | 0 |
| Cyclin D2 | | |
| 1 | 47 | 25 |
| 2 | 0 | 0 |
| 3 | 1 | 0 |
| 4 | 19 | 22 |
| 5 | 2 | 0 |
| HSD | 0 | 0 |
| 231 | 100 | 100 |
| Water | 0 | 0 |

The percentage of methylation (% M) was calculated as: (the number of copies of methylated DNA divided by the number of copies of unmethylated DNA+methylated DNA)×100, using absolute quantitation. The positive control for unmethylated DNA was human sperm DNA (HSD), and for methylated DNA was MDA MB231 (231).

Figure 5A:
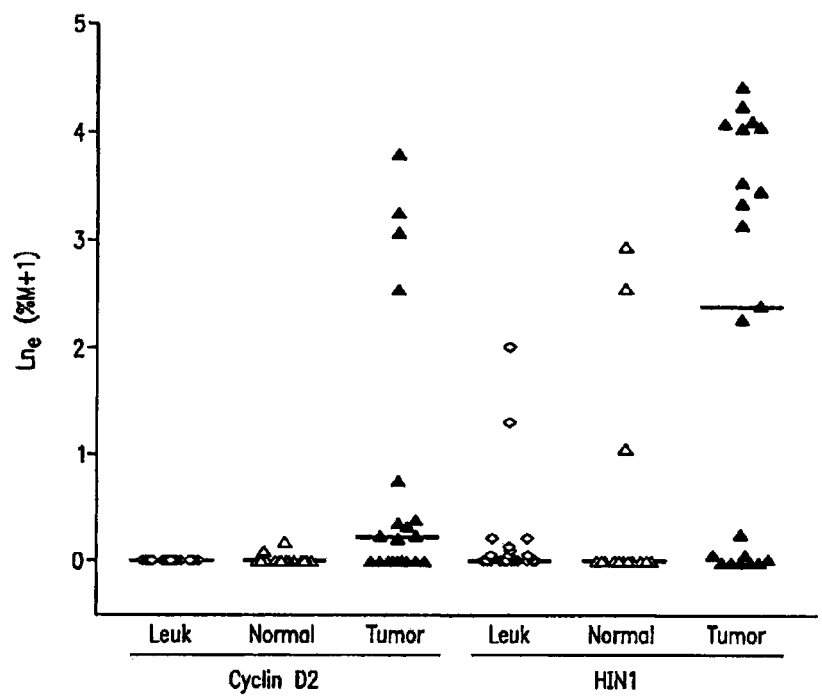
FIGS. 5A-B are scatter plots show the level of gene promoter hypermethylation in normal and malignant breast tissues as determined by the invention methods employing QM-MSP on normal tissues RASSF1A (n=28), TWIST (n=18) (FIG. 5A), Cyclin D2 (n=16), and HIN1 (n=14) (FIG. 5B) and DNA derived from individuals with invasive ductal carcinoma RASSF1A (n=19), TWIST (n=21), Cyclin D2 (n=21), and HIN1 (n=21) compared to leukocyte (Leuk) DNA derived from normal individuals (n=25). Displayed is the $Ln_e$ (% M+1). A bar indicates the median of each group.
Figure 5B:
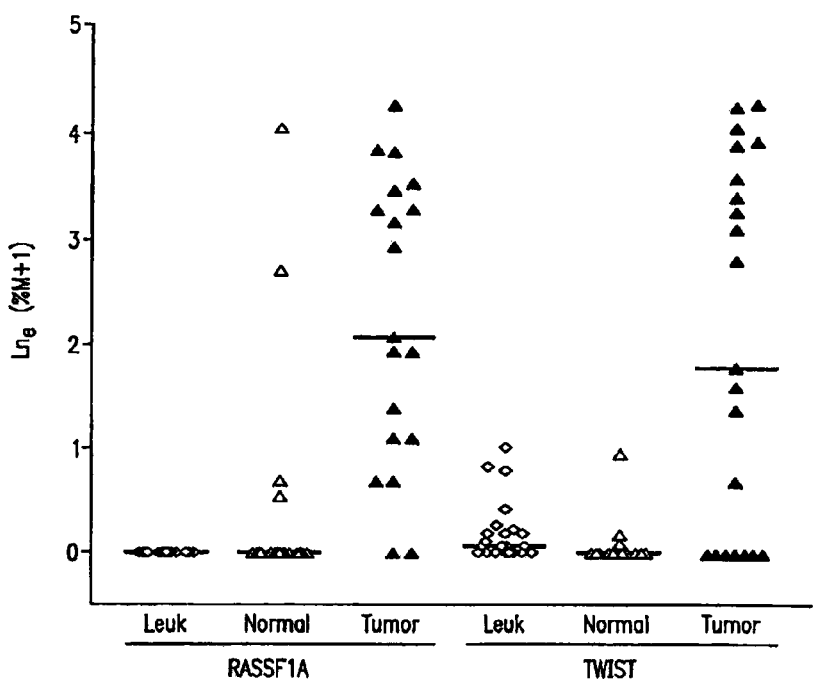
Figure 6B:
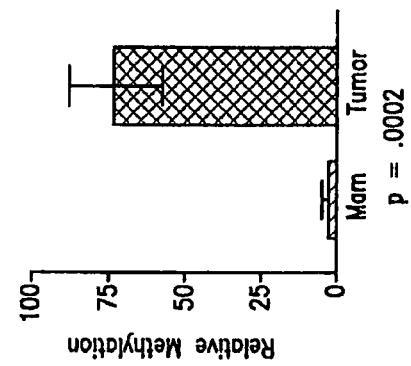
FIGS. 6A-B are bar graphs showing cumulative promoter hypermethylation of RASSF1A, TWIST, Cyclin D2, and HIN1 in normal and malignant breast tissues as determined by the invention methods as described in Table 5.
Figure 6A:
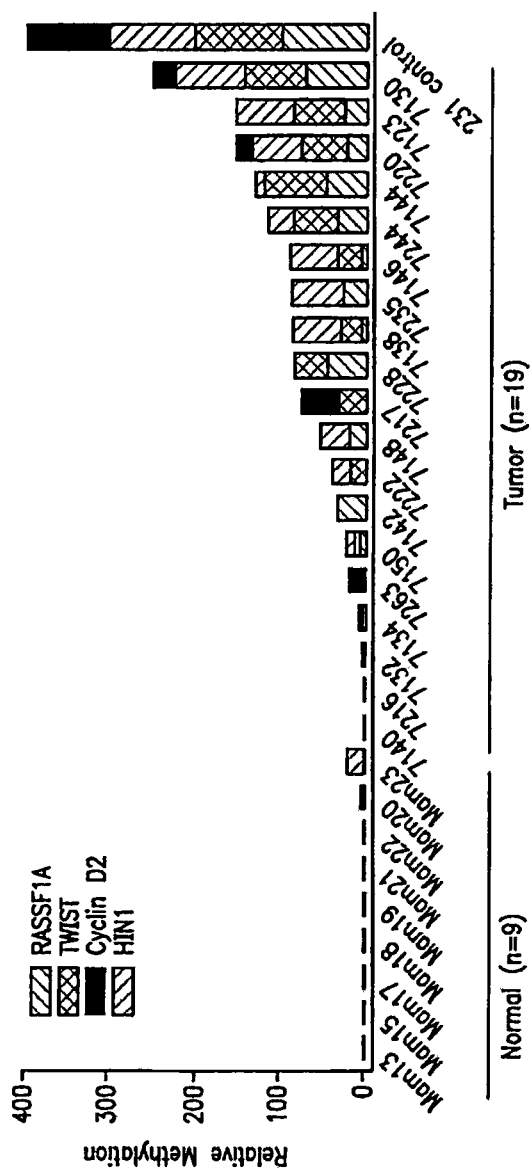

Quantitation of Methylation in Breast Carcinoma and Comparison to Normal Breast Tissue Paraffin-embedded, formalin-fixed tissues from routine reduction mammoplasty (14 to 28 samples each) and frozen primary breast carcinoma tissues (19 to 21 samples each) were analyzed by QM-MSP for gene promoter hypermethylation of RASSF1A, TWIST, Cyclin D2, and HIN1 (Table 5, FIGS. 5A-B). Head to head comparison of DNA extracted from frozen or fixed tissue showed no significant differences in methylation (data not shown). RASSF1A hypermethylation ranged from 0-71% (mean=18.5%) in tumors and 0-56% (mean=2.6%) in normal tissues (p=0.0001); TWIST hypermethylation ranged from 0-72% (mean=21.1%) in tumors and 0-1.6% (mean=0.11%) in normal tissues (p=0.0001); HIN1 hypermethylation ranged from 0-82.2% (mean=24.5%) in tumors, and 0-18% (mean=2.3%) in normal tissues (p=0.003); and Cyclin D2 hypermethylation ranged from 0-44.5% (mean=5.0%) in tumors, and 0-0.2% (mean=0.02%) in normal tissues (p=0.02). Highly significant differences in the medians were also present for all genes, RASSF1A (p=0.0001), TWIST (p=0.001), HIN1 (p=0.003), and Cyclin D2 (p=0.0009) (using the Mann-Whitney test on untransformed data).

A laboratory cutoff (% M) was established for each gene such that about 90-95% of normal breast tissues would be at or below the cutoff (Table 5). Using the cutoff of 2% M for RASSF1A and HIN1, 0.5% for TWIST, and 0.2% for Cyclin D2 in normal tissues, values above the cutoff were considered "positive" for hypermethylation. Among tumors, 68% (13 of 19) were positive for RASSF1A, 67% (14 of 21) for TWIST, 57% (12 of 21) for Cyclin D2, and 57% (12 of 21) for HIN1. By comparison, 7% (2 of 28) of normal mammoplasty samples were positive for RASSF1A, 6% (1 of 18) for TWIST, 7% (1 of 16) for Cyclin D2, and 14% (2 of 14) for HIN1. Some samples had low-level methylation that was below the cutoff. Using 0% M as a cutoff for each gene, tumor vs. normal hypermethylation was 89% positive vs. 7% for RASSF1A, 68% vs 17% for TWIST, 71% vs. 12% for Cyclin D2, and 76% vs. 21% for HIN1. Using these cutoffs, a significant difference in the incidences of positivity between tumor and normal tissues was observed (RASSF1A p<0.00002, TWIST p<0.0002, Cyclin D2 p<0.002, and HIN1 p<0.02; Fisher's exact).

TABLE 5

Normal versus Malignant Breast Tissues-Quantitation of the Level of Gene Promoter Hypermethylation

| Normal Breast | Range % | Median % | Mean ± SEM % | Lower 95% CI % | Upper 95% CI % | Positive for methylation[a] # (%) |
|---|---|---|---|---|---|---|
| RASSF1A | 0-56 | 0[b] | 2.6 ± 2.0 | (0) | 6.7 | 2/28 (7) |
| TWIST | 0-1.6 | 0[c] | 0.11 ± 0.09 | (0) | 0.29 | 1/18 (6) |

TABLE 5-continued

Normal versus Malignant Breast Tissues-Quantitation
of the Level of Gene Promoter Hypermethylation

| | | | | | | |
|---|---|---|---|---|---|---|
| HIN1 | 0-18 | 0[d] | 2.3 ± 1.5 | (0) | 5.5 | 2/14 (14) |
| Cyclin D2 | 0-0.2 | 0[e] | 0.019 ± 0.014 | (0) | 0.48 | 1/16 (7) |

| Breast Carcinoma | Range % | Median % | Mean ± SEM % | Lower 95% CI % | Upper 95% CI % | Positive for methylation[a] # (%) |
|---|---|---|---|---|---|---|
| RASSF1A | 0-71 | 7.0[b] | 18.5 ± 4.7 | 8.7 | 28.2 | 13/19 (68) |
| TWIST | 0-72 | 5.0[c] | 21.1 ± 5.5 | 9.6 | 32.6 | 14/21 (67) |
| HIN1 | 0-82 | 9.9[d] | 24.5 ± 6.1 | 11.8 | 37.3 | 12/21 (57) |
| Cyclin D2 | 0-44 | 0.26[e] | 5.0 ± 2.5 | (0) | 10.3 | 12/21 (57) |

[a]Based on cutoffs of 2% M for RASSF1A and HIN1, 0.5% M for TWIST, and 0.2% M for Cyclin D2;
[b]p = 0.0001 for RASSF1A,
[c]p = 0.001 for TWIST,
[d]p = 0.003 for HIN1, and
[e]p = 0.0009 for Cyclin D2.

Cumulative Gene Promoter Hypermethylation Scores in Primary Breast Cancer

To determine the cumulative amount of gene promoter hypermethylation, QM-MSP was performed and the sum of all % M within the panel of genes was used to provide an overall cumulative score for each sample. This was represented graphically relative to MDA-MB231 DNA, which is 100% methylated for RASSF1A, TWIST, Cyclin D2 and HIN1. Therefore, this control DNA has a relative score of 400 in FIG. 6A. The cumulative methylation profiles of nine normal mammoplasty samples were compared to those of 19 invasive tumors (Table 6; FIG. 6). Normal tissues ranged from 0-18 units, and tumors ranged from 1-248. Among the nine normal tissues tested for four genes (36 values) the cumulative score had a mean of 2.61±2.05 (median=0) (FIG. 6B). Among the 19 tumors tested for four genes (76 values) the cumulative score had a mean of 72.8±15.03 units (median=74) out of a possible 400 units (as above, Table 6 and FIGS. 6A and 6B). The difference in log-transformed means between normal and malignant breast tissue was highly significant (p-0.0001, unpaired t test with Welch's correction).

We explored the use of 4.7 units as a cumulative score cutoff value. This was based on the individual gene cutoffs above (2% each for RASSF1A and HIN1, 0.5% for TWIST and 0.2% for Cyclin D2=4.7%). Using this cutoff, 84% (16) tumor samples were positive. Although 3 of 19 tumors fell below the cutoff, all of the "negative" tumors were methylated at low levels for one or more genes in this panel (FIG. 6A). Among normal samples, 89% (8) were negative. Thus in this group of 28 samples (9 normal and 19 tumor), the sensitivity of detection of tumor was 0.84 and specificity was 0.89, an overall accuracy of 0.86 (24 of 28)

TABLE 6

Cumulative promoter hypermethylation in normal, adjacent "normal" and malignant breast tissues.

| Tissue | Range Units[a] | Median Units[a] | Mean ± SEM Units[a] | Lower 95% CI units[a] | Upper 95% CI units[a] | Positive for methylation[b] # (%) | n |
|---|---|---|---|---|---|---|---|
| Normal | 0-18 | 0[c] | 2.61 ± 2.05[d] | (0) | 7.35 | 1/9 (11) | 9 |
| Carcinoma | 0-248 | 74[c] | 72.8 ± 15.03[d] | 41.3 | 104.4 | 16/19 (84) | 19 |

Normal Mammoplasty and Malignant Breast Tissues
Comparison of Paired Tumor and Adjacent Normal Breast Epithelium

| Tissue | Range Units* | Median Units* | Mean ± SEM Units* | Lower 95% CI units* | Upper 95% CI units* | Positive for methylation[§] # (%) | n |
|---|---|---|---|---|---|---|---|
| Adjacent "Normal" | 2-29 | 9[e] | 11.7 ± 4.07 | 1.2 | 22.1 | 4/6 (67) | 6 |
| Carcinoma | 5-258 | 133[e] | 129.2 ± 39.9 | 26.5 | 231.8 | 6/6 (100) | 6 |

[a]Relative units of methylation is the sum of percent methylation for each of four genes in the panel;
[b]Based on a cutoff of ≤4.7 units.
[c]p = 0.0001,
[d]p = 0.0002;
[e]p = 0.03.

Figure 7C:
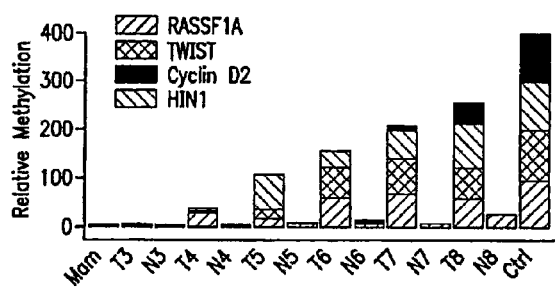
FIGS. 7A-B are bar graphs showing cumulative promoter hypermethylation of RASSF1A, TWIST, Cyclin D2, and HIN1 in adjacent normal and malignant breast tissues as described in Table 6.
Figure 7C:
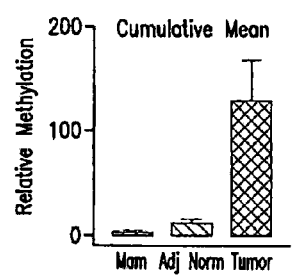

In an independent experiment, six pairs of tumor and adjacent tissue from the surgical margins, which were histologically normal, were examined to determine the cumulative amount of gene promoter hypermethylation in RASSF1A, TWIST, Cyclin D2, and HIN1 (Table 65, FIG. 7). The cumulative methylation ranged from 2-29 units within adjacent normal tissues and 5-258 units within tumor tissues, out of a possible 400 units (FIG. 7). Using the cutoff established for cumulative normal in mammoplasty samples (≤4.7 units, see above), all six tumors were positive. The adjacent "normal" tissues were also positive in four of six individuals. While the cumulative methylation levels within adjacent "normal" tissues were significantly lower than the nearby tumor (p=0.03 by Mann-Whitney), the tumor-adjacent tissues had a significantly higher level of methylation than normal mammoplasty samples (p=0.01 by Mann-Whitney; Table 6 and FIG. 7).

Detection of Multi-Gene Promoter Hypermethylation in Breast Duct Cells

Figure 8:
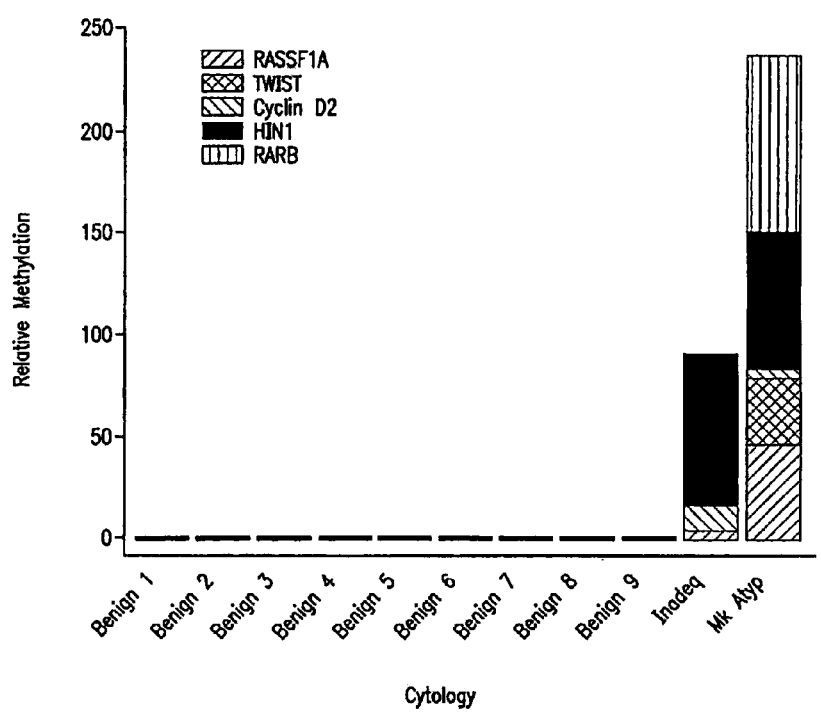
FIG. 8 is a bar graph showing cumulative promoter hypermethylation in ductal cells obtained by ductal lavage for RARB, RASSF1A, TWIST, Cyclin D2, and HIN1 genes determined using the invention methods as described in Table 7. Shown is the cumulative methylation of 50-1000 cells found in cytologically benign (n=7) and pre-invasive (DCIS; n=4) samples. For each patient sample the cytology was graded as having mild, moderate or marked atypia, or was found inadequate if fewer than 10 epithelial cells were observed. The relative level of methylation of each gene is indicated by the height of the bar. Total possible units=500 (5 genes×100%).

To test the applicability of this test to small clinical samples, we extracted DNA from ductal lavage (DL) cells that had been scraped from cytospin preparations after cytological evaluation and performed QM-MSP to test for RASSF1A, TWIST, Cyclin D2, RAR-β, and HIN1 gene promoter hypermethylation (Table 7, FIG. 8). The total number of epithelial cells present in the samples varied from 50-1000. The level of gene promoter methylation was quantitated for each sample and the cumulative promoter methylation profile was established. High level hypermethylation was detected in two of four cases of DCIS. Among diagnostically benign samples, six of seven showed no cumulative hypermethylation at all, compared to one of seven which revealed low level RASSF1A methylation (Table 7 and FIG. 8).

TABLE 7

Quantitative multiplexed methylation-specific PCR analysis of ductal breast cells

| | | % Methylation | | | | | |
|---|---|---|---|---|---|---|---|
| ID | RASSF1A | TWIST | Cyclin D2 | HIN1 | RARB | | |
| Ductal Lavage Cells From High Risk Women[a] | | | | | | Cytology | Mammography |
| 1 | 0 | 0 | 0 | 0 | 0 | Benign | Normal |
| 2 | 0 | 0 | 0 | 0 | 0 | Benign | Normal |
| 3 | 0 | 0 | 0 | 0 | 0 | Benign | Normal |
| 4 | 0 | 0 | 0 | 0 | 0 | Benign | Normal |
| 5 | 0 | 0 | 0 | 0 | 0 | Benign | Normal |
| 6 | 0 | 0 | 0 | 0 | 0 | Benign | Normal |
| 7 | 0.4 | 0 | 0 | 0 | 0 | Benign | Normal |
| Ductal Lavage Cells From Women With Carcinoma[b] | | | | | | Cytology | Histopathology |
| 8 | 0 | 0 | 0 | 0 | 0 | Benign | DCIS |
| 9 | 0 | 0 | 0 | 0 | 0 | Benign | DCIS |
| 10 | 4 | 0 | 12 | 75 | 0 | Inadequate | Invasive Carcinoma |
| 11 | 47 | 31 | 4 | 65 | 89 | Markedly atypical | Invasive Carcinoma | tumor-specific loss of NES1/kallikrein 10 expression. *Cancer Res* (2001) 61:8014-8021.
10. Yunes M J, Neuschatz A C, Bornstein L E, Naber S P, Band V, and Wazer D E: Loss of expression of the putative tumor suppressor NES1 gene in biopsy-proven ductal carcinoma in situ predicts for invasive carcinoma at definitive surgery. *Int J Radiat Oncol Biol Phys* (2003), 56: 653-657.
11. Kashiwaba M, Tamura G, and Ishida M: Aberrations of the APC gene in primary breast carcinoma. *J Cancer Res Clin Oncol* (1994) 120:727-731.
12. Virmani A K, Rathi A, Sathyanarayana U G, Padar A, Huang C X, Cunnigham H T, Farinas A J, Milchgrub S, Euhus D M, Gilcrease M, Herman J, Minna J D, and Gazdar A F: Aberrant methylation of the adenomatous polyposis coli (APC) gene promoter 1A in breast and lung carcinomas. *Clin Cancer Res* (2001) 7:1998-2004.
13. Sarrio D, Moreno-Bueno G, Hardisson D, Sanchez-Estevez C, Guo M, Herman J G, Gamallo C, Esteller M, and Palacios J: Epigenetic and genetic alterations of APC and CDH1 genes in lobular breast cancer: relationships with abnormal E-cadherin and catenin expression and microsatellite instability. *Int J Cancer* (2003) 106:208-215.

REFERENCE LIST

1. Hanahan D and Weinberg R A: The hallmarks of cancer. *Cell* (2000) 100:57-70.
2. Wamecke P M and Bestor T H: Cytosine methylation and human cancer. *Curr Opin Oncol* (2000) 12:68-73.
3. Yang X, Yan L, and Davidson N E: DNA methylation in breast cancer. *Endocr Relat Cancer* (2001) 8:115-127.
4. Widschwendter M and Jones P A: DNA methylation and breast carcinogenesis. *Oncogene* (2002) 21:5462-5482.
5. Wajed S A, Laird P W, and DeMeester T R: DNA methylation: an alternative pathway to cancer. *Ann Surg* (2001) 234:10-20.
6. Jones P A and Baylin S B: The fundamental role of epigenetic events in cancer. *Nat Rev Genet* (2002) 3:415-428.
7. Goyal J, Smith K M, Cowan J M, Wazer D E, Lee S W, and Band V: The role for NES I serine protease as a novel tumor suppressor. *Cancer Res* (1998) 58:4782-4786.
8. Dhar S, Bhargava R, Yunes M, Li B, Goyal J, Naber S P, Wazer D E, and Band V: Analysis of normal epithelial cell specific-1 (NES1)/kallikrein 10 mRNA expression by in situ hybridization, a novel marker for breast cancer. *Clin Cancer Res* (2001) 7:3393-3398.
9. Li B, Goyal J, Dhar S, Dimri G, Evron E, Sukumar S, Wazer D E, and Band V: CpG methylation as a basis for breast
14. Evron E, Umbricht C B, Korz D, Raman V, Loeb D M, Niranjan B, Buluwela L, Weitzman S A, Marks J, and Sukumar S: Loss of Cyclin D2 expression in the majority of breast cancers is associated with promoter hypermethylation. *Cancer Res* (2001) 61:2782-2787.
15. Lehmann U, Langer F, Feist H, Glockner S, Hasemeier B, and Kxeipe H: Quantitative assessment of promoter hypermethylation during breast cancer development. *Am J Pathol* (2002) 160:605-612.
16. Widschwendter M, Berger J, Hermann M, Muller H M, Amberger A, Zeschnigk M, Widschwendter A, Abendstein B, Zeimet A G, Daxenbichler G, and Marth C: Methylation and silencing of the retinoic acid receptor-beta2 gene in breast cancer. *J Natl Cancer Inst* (2000) 92:826-832.
17. Yan L, Yang X, and Davidson N E: Role of DNA methylation and histone acetylation in steroid receptor expression in breast cancer. *J Mammary Gland Biol Neoplasia* (2001) 6:183-192.
18. Sirchia S M, Ren M, Pili R, Sironi E, Somenzi G, Ghidoni R, Toma S, Nicolo G, and Sacchi N: Endogenous reactivation of the RARbeta2 tumor suppressor gene epigenetically silenced in breast cancer. *Cancer Res* (2002) 62:2455-2461.

19. Evron E, Dooley W C, Umbricht C B, Rosenthal D, Sacchi N, Gabrielson E, Soito A B, Hung D T, Ljung B, Davidson N E, and Sukumar S: Detection of breast cancer cells in ductal lavage fluid by methylation-specific PCR. *Lancet* (2001) 357:1335-1336.
20. Burbee D G, Forgacs E, Zochbauer-Muller S, Shivakumar L, Fong K, Gao B, Randle D, Kondo M, Virmani A, Bader S, Sekido Y, Latif F, Milchgrub S, Toyooka S, Gazdar A F, Lerman M I, Zabarovsky E, White M, and Minna J D: Epigenetic inactivation of RASSF1A in lung and breast cancers and malignant phenotype suppression. *J Natl Cancer Inst* (2001) 93:691-699.
21. Dammann R, Yang G, and Pfeifer G P: Hypermethylation of the cpG island of Ras association domain family 1A (RASSF1A), a putative tumor suppressor gene from the 3p21.3 locus, occurs in a large percentage of human breast cancers. *Cancer Res* (2001) 61:3105-3109.
22. Krop I E, Sgroi D, Porter D A, Lunetta K L, LeVangie R, Seth P, Kaelin C M, Rhei E, Bosenberg M, Schnitt S, Marks J R, Pagon Z, Belina D, Razumovic J, and Polyak K: HIN-1, a putative cytokine highly expressed in normal but not cancerous mammary epithelial cells. *Proc Natl Acad Sci USA* (2001) 98:9796-9801.
23. Fackler M J, McVeigh M, Evron E, Garrett E, Mehrotra J, Polyak L, Sukumar S, and Argani P: DNA methylation of RASSF1A, HIN-1, RAR-beta, Cyclin D2 and TWIST in in situ and invasive lobular breast carcinoma. *Int J Cancer* (2003), (in press, online).
24. Fackler M J, Evron E, Khan S A, and Sukumar S: Novel agents for chemoprevention, screening methods, and sampling issues. *J Mammary Gland Biol Neoplasia* (2003) 8:75-89.
25. Tsou J A, Hagen J A, Carpenter C L, and Laird-Offringa I A: DNA methylation analysis: a powerful new tool for lung cancer diagnosis. *Oncogene* (2002) 21:5450-5461.
26. Muller H M and Widschwendter M: Methylated DNA as a possible screening marker for neoplastic disease in several body fluids. *Expert Rev Mol Diagn* (2003) 3:443-58.
27. Cottrell S E and Laird P W: Sensitive detection of DNA methylation. *Ann NY Acad Sci* (2003) 983:120-130.
28. Herman J G, Graff J R, Myohanen S, Nelkin B D, and Baylin S B: Methylation-specific PCR: a novel PCR assay for methylation status of CpG islands. *Proc Natl Acad Sci USA* (1996) 93:9821-9826.
29. Palmisano W A, Divine K K, Saccomanno G, Gilliland F D, Baylin S B, Hennan J G, and Belinsky S A: Predicting lung cancer by detecting aberrant promoter methylation in sputum. *Cancer Res* (2000) 60:5954-5958.
30. Buller A, Pandya A, Jackson-Cook C, Bodurtha J, Tekin M, Wilkinson D S, Garrett C T, and Feneira-Gonzalez A: Validation of a multiplex methylation-sensitive PCR assay for the diagnosis of Prader-Willi and Angelman's syndromes. *Mol Diagn* (2000) 5:239-243.
31. Brock M V, Gou M, Akiyama Y, Muller A, Wu T T, Montgomery E, Deasel M, Germonpre P, Rubinson L, Heitmiller R F, Yang S C, Forastiere A A, Baylin S B, and Herman J G: Prognostic importance of promoter hypermethylation of multiple genes in esophageal adenocarcinoma. *Clin Cancer Res* (2003) 9:2912-2919.
32. Trinh B N, Long T I, and Laird P W: DNA Methylation Analysis by MethyLight Technology. *Methods* (2001) 25:456-462.
33. Jeronimo C, Usadel H, Henrique R, Silva C, Oliveira J, Lopes C, and Sidransky D: Quantitative GSTP1 hypermethylation in bodily fluids of subjects with prostate cancer. *Urology* (2002) 60:1131-1135.
34. Califano J, van der RP, Westra W, Nawroz H, Clayman G, Piantadosi S, Corio R, Lee D, Greenberg B, Koch W, and Sidransky D: Genetic progression model for head and neck cancer: implications for field cancerization. *Cancer Res* (1996) 56:2488-2492.
35. Umbricht C B, Evron E, Gabrielson E, Ferguson A, Marks J, and Sukumar S: Hypermethylation of 14-3-3 sigma (stratifin) is an early event in breast cancer. *Oncogene* (2001) 20:3348-3353.
36. Deng G, Lu Y, Zlotnikov G, Thor A D, and Smith H S: Loss of heterozygosity in normal tissue adjacent to breast carcinomas. *Science* (1996) 274:2057-2059.
37. Heid C A, Stevens J, Livak K J, and Williams P M: Real time quantitative PCR. *Genome Res* (1996) 6:986-94.
38. Gibson U E, Heid C A, and Williams P M: A novel method for real time quantitative RT-PCR. *Genome Res* (1996) 6:995-1001.
39. Lo Y M, Wong I H, Zhang J, Tein M S, Ng M H, and Hjelm N M: Quantitative analysis of aberrant p16 methylation using real-time quantitative methylation-specific polymerase chain reaction. *Cancer Res* (1999) 59:3899-903.
40. Wong I H, Zhang J, Lai P B, Lau W Y, and Lo Y M: Quantitative analysis of tumor-derived methylated p16INK4a sequences in plasma, serum and blood cells of hepatocellular carcinoma subjects. *Clin Cancer Res* (2003) 9:1047-52.
41. Frank Lyko: DNA methylation learns to fly. *Trends in Gen* (2001) 17:169-72.
42. Finnegan E J, Genger R K, Peacock W J, and Dennis E S: DNA methylation in plants. *Annu Rev Plant Physiol Plant Mol Biol* (1998) 49: 223-247.
43. Hueller H M, Ivarsson L, Schrocksnadel H, Fiegl H, Widschwendter A, Goebel G, Kilga-Nogler S, Philadelphy H, Gutter W, Marth C and Widschwendter M.: DNA methylation changes in sera of women in early pregnancy are similar to those in advance breast cancer subjects. *Clin Chem* (2004) 50:1065-1068.
44. Fackler M J, McVeigh M, Mehrotra J, Blum M A, Lange J, Lapides A, Garrett E, Argani P, and Sukumar S.: Quantitative multiplex methylation-specific PCR assay for the detection of promoter hypermethylation in multiple genes in breast cancer. *Cancer Res* (2004) 64:4442-4452.

Although the invention has been described with reference to the above example, it will be understood that modifications and variations are encompassed within the spirit and scope of the invention. Accordingly, the invention is limited only by the following claims.

What is claimed is:

1. A method of diagnosing development of a condition associated with aberrant methylation of DNA in tissue or other DNA sample of a subject, said method comprising:
   a) co-amplifying DNA in a subject sample comprising a plurality of different DNA sequences isolated from the tissue using a mixture of DNA sequence-specific, methylation status-independent outer primer pairs that selectively hybridize to one or more of the DNA sequences under conditions that allow generation of a first amplification product containing first amplicons;
   b) co-amplifying the first amplicons by real-time PCR under conditions that allow generation of one or more second amplification products; adding one or more members of a set of DNA sequence-specific probes comprising an optically detectable label and one or more members of a set of DNA sequence-specific methylation status-dependent inner primer pairs, wherein the probes and the inner primer pairs selectively hybridize cognate first amplicons, and wherein the sets of probes and inner primer pairs collectively bind to a plurality of different first amplicons in the first amplification product;
   c) detecting signal intensity of the optical label in the second amplification products to determine the amount of methylation of the second amplification products, wherein sensitivity of detecting methylated versus unmethylated amplicons is at least 1 in 100,000; and
   d) deriving a combined methylation value for the methylation in the tissue of the subject from amounts of methylation determined for the second amplification products as compared with a combined methylation value in comparable normal tissue to diagnose the state of development of the condition in the subject.

2. The method of claim 1, wherein d) comprises determining cumulative detected signal intensity from the second amplification gene products to measure a cumulative amount of gene promoter hypermethylation in the tissue of the subject as compared with a cumulative amount of methylation in comparable normal tissue to diagnose the state of development of the condition in the subject.

3. The method of claim 1, wherein the probes are molecular beacons or bilabeled oligonucleotide probes comprising a fluorescent moiety and a quencher moiety.

4. The method of claim 1, wherein the condition is a cancer and the subject tissue is associated with the cancer.

5. A method of diagnosing development of a cancer associated with hypermethylation of CpG islands in cancer-associated tissue of a subject, said method comprising:
   a) co-amplifying CpG islands in a subject sample comprising a plurality of different DNA sequences isolated from the carcinoma-associated tissue using a mixture of DNA sequence-specific, methylation status-independent outer primer pairs that selectively hybridize to cognate DNA sequences under conditions that allow generation of a first amplification product containing first amplicons;
   b) using real time PCR to co-amplify CpG islands in the first amplicons under conditions that allow generation of one or more second amplification products, using one or more members of a set of DNA sequence-specific probes comprising one or more fluorescent moieties and one or more members of a set of DNA sequence-specific methylation status-dependent inner primer pairs that selectively hybridize to one or more first amplicons, wherein the sets of probes and inner primer pairs collectively hybridize to a plurality of different first amplicons in the first amplification product;
   c) detecting fluorescence due to the presence of the fluorescent moieties in the second amplification products to determine the amount of methylation of the CpG islands therein, wherein sensitivity of detecting methylated versus unmethylated amplicons is at least 1 in 100,000; and
   d) deriving a combined methylation value for the CpG islands in the DNA sequences from amounts of methylation determined for the second amplification products as compared with the combined methylation value in a comparable normal DNA sample to diagnose the state of development of the cancer in the subject.

6. The method of claim 5, wherein d) comprises determining cumulative detected fluorescence from the second amplification products to measure a cumulative amount of gene promoter hypermethylation in the DNA of the tissue of the subject as compared with a cumulative amount of methylation in the DNA of comparable normal tissue to diagnose the state of development of the cancer in the subject.

7. The method of claim 5, additionally comprising adding an internal standard in b) for assessing relative amounts of hypermethylation in CpG islands in the DNA sequences after amplification.

8. The method of claim 5, wherein the combined methylation value of the CpG islands is correlated to the development of the cancer in the subject by comparing the amount of amplification of the CpG islands to the amount of amplification product formed from known standards.

9. The method of claim 8, wherein the standards are MDA-MB231 cell DNA and human sperm DNA or similarly methylated or unmethylated DNA.

10. The method of claim 5, wherein the DNA sequences comprise a regulatory region.

11. The method of claim 10, wherein the regulatory region is a promoter.

12. The method of claim 5, further comprising using the level of unmethylated CpG island in the second amplification products as the internal control for assessing the extent of methylated CpG island present.

13. The method of claim 5, wherein the carcinoma is selected from a breast cancer, a colon cancer, an esophageal cancer, a pancreatic cancer, a liver cancer, a skin cancer, an ovarian cancer, an endometrial cancer, a prostate cancer, a kidney cancer, a lung cancer, a bronchial cancer, a bladder cancer or a lymphoma, a hematopoietic tumor, a leukemia, a muscle cancer, a bone cancer, or a brain cancer, either as a primary or as metastasis in distant organs.

14. The method of claim 5, wherein fluorescence is separately detected from the fluorescent moieties in separate aliquots of the first amplification product to indicate methylation status of the second amplicons in the separate aliquots.

15. The method of claim 5, wherein the subject sample is ductal lavage fluid.

16. The method of claim 5, wherein the subject sample comprises two or more selected from ductal lavage fluid, nipple aspiration fluid, blood, plasma, lymph, duct cells, breast tissue, lymph nodes, liver, lung, or brain and bone marrow metastasis.

17. The method of claim 5, wherein the isolated DNA sequences are selected from RASSF1A, TWIST, Cyclin D2, RAR-β, HIN1, ESR1, APC1, BRCA1, BRCA2, and HIC1 promoters.

18. The method of claim 17, wherein the first external primer pairs in a) are selected from SEQ ID NOS:1-12 and 46-57.

19. The method of claim 5, wherein in b) members of the set of second primer pairs selectively hybridize to first amplicons containing methylation of a CpG island and b) is repeated using an additional set of second primer pairs that selectively hybridize to amplicons containing unmethylation of a CpG island in the first amplicons.

20. The method of claim 18, wherein the second internal primer pairs in used b) are selected from DNA sequences having nucleotide sequences of SEQ ID NOS: 13, 14, 16, 17, 19, 20, 22, 23, 25, 26, 28, 29, 31, 32, 34, 35, 37, 38, 40, 41, 58, 59, 61, 62, 64, 65, 67, 68, 70, 71, 73, 74, 76, 77, 79, 80, 82, 83, 85, 86, 88, 89, 91 and 92, and the probes are selected from DNA sequences having nucleotides sequences of SEQ ID NOS: 15, 18, 21, 24, 27, 30, 33, 36, 39, 42, 60, 63, 66, 69, 72, 75, 78, 81, 84, 87, 90 and 93.

21. A method for determining the methylation status of a DNA sample comprising:

a) co-amplifying a plurality of DNA sequences obtained from a subject sample using a mixture of DNA sequence-specific, methylation status-independent outer primer pairs that selectively hybridize to one of the DNA sequences under conditions that allow generation of a first amplification product containing first amplicons;

b) using quantitative PCR to amplify first amplicons under conditions that allow generation of second amplification products, using a set of DNA sequence-specific, methylation status-dependent inner primer pairs and a set of DNA sequence-specific probes comprising one or more distinguishable optically detectable labels, wherein a combination of inner primer pair and probe selectively hybridizes to one first amplicon, and wherein the sets of inner primer pairs and probes collectively hybridize to a plurality of first amplicons in the first amplification product;

c) detecting signal intensities of the one or more distinguishable labels in the second amplification products to determine the amount of methylation of the second amplification products, wherein sensitivity of detecting methylated versus unmethylated amplicons is at least 1 in 100,000; and d) deriving a combined methylation value for the methylation in the DNA sequences from amounts of methylation determined for the second amplification products as compared with the combined methylation value in a comparable normal DNA sample to determine the methylation status of the DNA sample.

* * * * *